US012186314B2

(12) United States Patent
Patwardhan et al.

(10) Patent No.: US 12,186,314 B2
(45) Date of Patent: Jan. 7, 2025

(54) COMPOSITIONS AND METHODS FOR TREATMENT, AMELIORATION, AND PREVENTION OF ANESTHESIA-INDUCED HYPOTHERMIA

(71) Applicants: ARIZONA BOARD OF REGENTS ON BEHALF OF THE UNIVERSITY OF ARIZONA, Tucson, AZ (US); DIGNITY HEALTH, San Francisco, CA (US)

(72) Inventors: Amol Patwardhan, Tucson, AZ (US); Frank Porreca, Tucson, AZ (US); Andrej Romanovsky, Phoenix, AZ (US)

(73) Assignees: ARIZONA BOARD OF REGENTS ON BEHALF OF THE UNIVERSITY OF ARIZONA, Tucson, AZ (US); DIGNITY HEALTH, San Francisco, CA (US)

(*) Notice: Subject to any disclaimer, the term of this patent is extended or adjusted under 35 U.S.C. 154(b) by 0 days.

(21) Appl. No.: 16/065,441

(22) PCT Filed: Dec. 20, 2016

(86) PCT No.: PCT/US2016/067825
§ 371 (c)(1),
(2) Date: Jun. 22, 2018

(87) PCT Pub. No.: WO2017/112693
PCT Pub. Date: Jun. 29, 2017

(65) Prior Publication Data
US 2019/0008865 A1 Jan. 10, 2019

Related U.S. Application Data

(60) Provisional application No. 62/271,048, filed on Dec. 22, 2015.

(51) Int. Cl.
*A61K 31/506* (2006.01)
*A61K 9/00* (2006.01)
*A61K 31/165* (2006.01)
*A61K 31/357* (2006.01)
*A61K 31/416* (2006.01)
*A61K 31/55* (2006.01)
*A61M 16/01* (2006.01)
*A61P 43/00* (2006.01)

(52) U.S. Cl.
CPC .......... *A61K 31/506* (2013.01); *A61K 9/0019* (2013.01); *A61K 9/0053* (2013.01); *A61K 31/165* (2013.01); *A61K 31/357* (2013.01); *A61K 31/416* (2013.01); *A61K 31/55* (2013.01); *A61P 43/00* (2018.01); *A61M 16/01* (2013.01)

(58) Field of Classification Search
CPC .. A61K 31/165; A61K 31/357; A61K 31/416; A61K 31/506; A61K 31/55; A61K 9/0019; A61K 9/0053; A61M 16/01; A61P 43/00
See application file for complete search history.

(56) References Cited

U.S. PATENT DOCUMENTS 8,367,733 B2    2/2013  Burch et al.
2011/0104301 A1* 5/2011  Ahern ............... A61K 31/7105
                                                    424/617

FOREIGN PATENT DOCUMENTS

WO    WO 2015/044759    4/2015

OTHER PUBLICATIONS

McGaraughty et al. 2009, Brain Research, 1268:58-67. (Year: 2009).*
Uchytilova et al. Nov. 17, 2014, Molecular Pain, 10:67 First Published Jan. 1, 2014. (Year: 2014).*
Tamayo et al. J. Med. Chem, 2008, 51, 2744-2757. (Year: 2008).*
Othman et al. British Journal of Clinical Pharmacology, 75:4, 2012 pp. 1029-1040. (Year: 2012).*
Zeller et al. BMC Pharmacology, 2007, 7:2, pp. 1-12. (Year: 2007).*
Gavva et al. The Journal of Neuroscience, 2007, 27(13):3366-3374. (Year: 2007).*
Aronoff, DM, et al., Eicosanoids in non-febrile thermoregulation. Prog Brain Res. 2007;162:15-25.
Baker, N., et al. Infection control hazards of intraoperative forced air warming. J Hosp Infect. Jun. 2002;51(2):153-4.
Barabas, M.E., et al., TRPV1, but not TRPA1, in primary sensory neurons contributes to cutaneous incision mediated hypersensitivity Mol Pain, 2013. 9:9.
Brennan, T.J., et al., Characterization of a rat model of incisional pain. Pain. Mar. 1996;64(3):493-501.
Brennan, T.J., et al., Pathophysiology of postoperative pain. Pain. Mar. 2011;152(3 Suppl): S33-40. doi: 10.1016/j.pain.2010.11.005. Epub Jan. 12, 2011.
Butwick, A.J., et al., Intraoperative forced air-warming during cesarean delivery under spinal anesthesia does not prevent maternal hypothermia. Anesth Analg. Nov. 2007;105(5):1413-9, table of contents.
Cavanaugh, D.J., et al., Trpv1 reporter mice reveal highly restricted brain distribution and functional expression in arteriolar smooth muscle cells. J Neurosci. Mar. 30, 2011;31(13):5067-77.
Chaplan, S.R., et al., Quantitative assessment of tactile allodynia in the rat paw. J Neurosci Methods. Jul. 1994;53(1):55-63.
Chizh, B.A., et al., The effects of the TRPV1 antagonist SB-705498 on TRPV1 receptor-mediated activity and inflammatory hyperalgesia in humans. Pain. Nov. 2007;132(1-2):132-41.
Chung, K., et al., Thermal burn injury associated with a forced-air warming device. Korean J Anesthesiol. Apr. 2012;62(4):391-2.
EP Search Report, EP Patent Application No. 16879985.6, mailed Dec. 13, 2019, 2 pages.

(Continued)

*Primary Examiner* — Kara R McMillian
(74) *Attorney, Agent, or Firm* — Snell & Wilmer L.L.P.

(57) ABSTRACT

Compositions and methods are provided for treating, ameliorating, and preventing anesthesia-induced hypothermia and/or postsurgical associated hyperalgesia in a mammalian subject comprising administering to the subject an effective amount of an ion channel TRPV1 inhibitor.

5 Claims, 7 Drawing Sheets

(56) References Cited

OTHER PUBLICATIONS

Frank, et al., Epidural versus general anesthesia, ambient operating room temperature, and patient age as predictors of inadvertent hypothermia. Anesthesiology. Aug. 1992;77(2):252-7.
Garami, et al., Contributions of different modes of TRPV1 activation to TRPV1 antagonist-induced hyperthermia. J Neurosci. Jan. 27, 2010;30(4):1435-40.
Gavva, N.R., Body-temperature maintenance as the predominant function of the vanilloid receptor TRPV1. Trends Pharmacol Sci. Nov. 2008;29(11):550-7.
Gavva, NR, et al., Pharmacological blockade of the vanilloid receptor TRPV1 elicits marked hyperthermia in humans. Pain. May 2008;136(1-2):202-10.
Gavva, NR, et al., Repeated administration of vanilloid receptor TRPV1 antagonists attenuates hyperthermia elicited by TRPV1 blockade. J Pharmacol Exp Ther. Oct. 2007;323(1):128-37.
Guignard, et al, Acute opioid tolerance: intraoperative remifentanil increases postoperative pain and morphine requirement. Anesthesiology. Aug. 2000;93(2):409-17.
Hargreaves, K., et al., A new and sensitive method for measuring thermal nociception in cutaneous hyperalgesia. Pain. Jan. 1988;32(1):77-88.
Honore, P. et al. Repeated dosing of ABT-102, a potent and selective TRPV1 antagonist, enhances TRPV1-mediated analgesic activity in rodents, but attenuates antagonist-induced hyperthermia. Pain. vol. 142, No. 1, pp. 27-35, Mar. 2009.
International Search Report & Written Opinion, International Patent Application No. PCT/US2016/067825, mailed Feb. 27, 2017, 15 pages.
Ivanov, AI, et al., Platelet-activating factor: a previously unrecognized mediator of fever. J Physiol. Nov. 15, 2003;553(Pt 1):221-8.
Julius, D., TRP channels and pain. Annu Rev Cell Dev Biol. 2013; 29:355-84.
Kehlet, H. et al., Effect of postoperative analgesia on surgical outcome. Br J Anaesth. Jul. 2001;87(1):62-72.
Kehlet, H., et al., Persistent postsurgical pain: risk factors and prevention. Lancet. May 13, 2006;367(9522):1618-25.
Leben, J. et al., Prevention of Hypothermia during Surgery—Contribution of Convective Heating System and Warm Infusion, Ann N Y Acad Sci, 1997. 813: p. 807-11.
Lin, E.P., et al., Wet forced-air warming blankets are ineffective at maintaining normothermia. Paediatr Anaesth. Jul. 2008;18(7):642-4.
Matsukawa, et al., Heat flow and distribution during epidural anesthesia. Anesthesiology. Nov. 1995;83(5):961-7.
McGaraughty, S. et al. Antagonism of TRPV1 receptors indirectly modulates activity of thermoregulatory neurons in the medial preoptic area of rats. Brian Research. vol. 1268. pp. 58-67, May 2009.
McGovern, P.D., et al., Forced-air warming and ultra-clean ventilation do not mix: an investigation of theatre ventilation, patient warming and joint replacement infection in orthopaedics. J Bone Joint Surg Br. Nov. 2011;93(11):1537-44.
Morimoto, A, et al., The effect of prostaglandin E2 on the body temperature of restrained rats. Physiol Behav. Jul. 1991;50(1):249-53.
Ni, D. et al. Effect of increasing temperature on TRPV1-mediated responses in isolated rat pulmonary sensory neurons. American Journal of Physiology—Lung Cellular and Molecular Physiology. vol. 294, No. 3, Mar. 2008, 9 pages.
Ohlson, KB, et al., Thermogenesis inhibition in brown adipocytes is a specific property of volatile anesthetics. Anesthesiology. Feb. 2003;98(2):437-48.
Patwardhan, A.M., et al., Heat generates oxidized linoleic acid metabolites that activate TRPV1 and produce pain in rodents. J Clin Invest. May 2010;120(5):1617-26.
Pogatzki-Zahn, E.M., et al., Heat hyperalgesia after incision requires TRPV1 and is distinct from pure inflammatory pain. Pain. Jun. 2005;115(3):296-307.

Rathmell, J.P., et al., Acute post-surgical pain management: a critical appraisal of current practice, Dec. 2-4, 2005. Reg Anesth Pain Med. Jul. -Aug. 2006;31(4 Suppl 1):1-42.
Romanovsky, AA, et al., Endotoxin shock: thermoregulatory mechanisms. Am J Physiol. Apr. 1996;270(4 Pt 2): R693-703.
Sessler, D.I., Forced-air warming in infants and children. Paediatr Anaesth. Jun. 2013;23(6):467-8. doi: 10.1111/pan.12177.
Sessler, D.I., Mild perioperative hypothermia. N Engl J Med. Jun. 12, 1997;336(24):1730-7.
Sessler, et al., Temperature monitoring and perioperative thermoregulation. Anesthesiology. Aug. 2008;109(2):318-38.
Souter, A.J., et al., Controversies in the perioperative use of nonsterodial antiinflammatory drugs. Anesth Analg. Dec. 1994;79(6):1178-90.
Steiner, AA, et al., Leptin: at the crossroads of energy balance and systemic inflammation. Prog Lipid Res. Mar. 2007;46(2):89-107.
Steiner, AA, et al., Nonthermal activation of transient receptor potential vanilloid-1 channels in abdominal viscera tonically inhibits autonomic cold-defense effectors. J Neurosci. Jul. 11, 2007;27(28):7459-68.
Szelenyi, Z, et al., Cholecystokinin octapeptide (CCK-8) injected into a cerebral ventricle induces a fever-like thermoregulatory response mediated by type B CCK-receptors in the rat. Brain Res. Feb. 28, 1994;638(1-2):69-77.
Tander, B., et al., Risk factors influencing inadvertent hypothermia in infants and neonates during anesthesia. Paediatr Anaesth. Jul. 2005;15(7):574-9.
Thomas, T., et al., Prediction and assessment of the severity of post-operative pain and of satisfaction with management. Pain. Apr. 1998;75(2-3):177-85.
Trevisani, M. et al. Targeting TRPV1: Challenges and Issues in Pain Management. The Open Drug Discovery Journal. vol. 2, pp. 37-49, 2010.
Uchytilova, E. et al. TRPV1 antagonist attentuates postoperative hypersensitivity by central and peripheral mechanisms. Molecular Pain 2014, 10:67, Nov. 2014, 25 pages.
Voight, et al., Discovery of (R)-1-(7-chloro-2,2-bis(fluoromethyl)chroman-4-yl)-3-(3-methylisoquinolin-5-yl)urea (A-1165442): a temperature-neutral transient receptor potential vanilloid-1 (TRPV1) antagonist with analgesic efficacy. J Med Chem. Sep. 11, 2014;57(17):7412-24.
White, P.F., The changing role of non-opioid analgesic techniques in the management of postoperative pain. Anesth Analg. Nov. 2005;101(5 Suppl): S5-22.
Wong, G.Y. et al., Therapeutic potential of vanilloid receptor TRPV1 agonists and antagonists as analgesics: Recent advances and setbacks. Brain Res Rev. Apr. 2009;60(1):267-77.
Woolf, C.J. et al., Preemptive analgesia—treating postoperative pain by preventing the establishment of central sensitization. Anesth Analg. Aug. 1993;77(2):362-79.
Woolf, C.J., Central sensitization: implications for the diagnosis and treatment of pain. Pain. Mar. 2011;152(3 Suppl): S2-15.
Wu, C., et al., Effect of AMG0347, a transient receptor potential type V1 receptor antagonist, and morphine on pain behavior after plantar incision. Anesthesiology. Jun. 2008;108(6):1100-8.
Zylan, KD, et al., Effect of ambient temperature on the paradoxical metabolic responses to norepinephrine. Pharmacol Biochem Behav. Oct. 1992;43(2):577-82.
International Search Report issued in PCT Application No. PCT/US16/67825 on Jun. 29, 2017.
Written Opinion issued in PCT Application No. PCT/US16/67825 on Jun. 29, 2017.
European Search Report issued in European Application No. 16879985.6 on Dec. 13, 2019.
European Search Report issued in European Application No. 16879985.6 on Sep. 3, 2020.
International Preliminary Report on Patentability dated Jun. 26, 2018 in corresponding International Application No. PCT/US2016/067825 filed Dec. 20, 2016; total 7 pages.
Patent Examination Report 1 issued Mar. 13, 2023 in corresponding New Zealand Patent Application No. 743894 filed Jun. 27, 2018; total 4 pages.
Patent Examination Report 2 issued Oct. 5, 2023 in corresponding New Zealand Patent Application No. 743894 filed Jun. 27, 2018; total 2 pages.

(56) References Cited

OTHER PUBLICATIONS

Patent Examination Report 3 issued Dec. 4, 2023 in corresponding New Zealand Patent Application No. 743894 filed Jun. 27, 2018; total 3 pages.
Australian Examination Report dated Jan. 18, 2022 in corresponding Australian Application No. 2016378556 filed Dec. 20, 2016; total 4 pages.

* cited by examiner

COMPOSITIONS AND METHODS FOR TREATMENT, AMELIORATION, AND PREVENTION OF ANESTHESIA-INDUCED HYPOTHERMIA

CROSS-REFERENCE TO RELATED APPLICATIONS

This application is a Section 371 U.S. national stage entry of International Patent Application No. PCT/US2016/067825, International Filing Date Dec. 20, 2016 which claims priority to and the benefit of U.S. Provisional Application No. 62/271,048, filed Dec. 22, 2015, which is hereby incorporated by reference in their entireties its entirety.

FIELD OF THE INVENTION

Compositions and methods are provided for treating, ameliorating, and preventing anesthesia-induced hypothermia and/or postsurgical associated hyperalgesia in a mammalian subject comprising administering to the subject an effective amount of an ion channel TRPV1 inhibitor.

INTRODUCTION

Anesthesia-induced hypothermia causes serious complications including coagulopathy (see, e.g., Rajagopalan, S, et al., Anesthesiology (2008) 108 71-7), surgical wound infections (see, e.g., Kurz, A, et al., N Engl J Med (1996) 334 1209-15), and perhaps myocardial complications (see, e.g., Frank, S M, JAMA (1997) 277 1127-34). It also decreases drug metabolism (see, e.g., Leslie, K, et al., Anesth Analg. (1995). 80 1007-14), prolongs recovery (see, e.g., Lenhardt, R, et al., Anesthesiology (1997) 87 1318-23), and provokes thermal discomfort (see, e.g., Kurz, A, et al., J Clin Anesth (1995) 7 359-66). It is thus now standard-of-care to warm surgical patients. Various guidelines, including the Surgical Care Improvement Project and National Institute of Health and Clinical Excellence, suggest that patients should be normothermic, defined as a core temperature of at least 36° C. at the end of surgery.

Approximately 50 million patients undergo surgical procedures each year in the United States (see, e.g., CDC, National Hospital Discharge Survey. 2010). Minimal postoperative pain, improvement of function and early release from hospital are important desired outcomes of these procedures (see, e.g., Becker, G. J., et al., Arch Surg, 1984. 119(11): p. 1338-42; Cheng, D. C., Anesthesiology, 1998. 88(6): p. 1429-33; Lenhardt, R., et al., Anesthesiology, 1997. 87(6): p. 1318-23). Diminishing inpatient time is significant both for the patient and economically for the health care system (see, e.g., Becker, G. J., et al., Arch Surg, 1984. 119(11): p. 1338-42).

Two of the major factors associated with delayed postoperative recovery and hospital release are postoperative pain and core body temperature homeostasis (see, e.g., Lenhardt, R., et al., Anesthesiology, 1997. 87(6): p. 1318-23; White, P. F., Anesth Analg, 2005. 101(5 Suppl): p. S5-22). Controlling perioperative core body temperature is a critical factor that leads to successful postsurgical recovery (see, e.g., Lenhardt, R., et al., Anesthesiology, 1997. 87(6): p. 1318-23; Kurz, A., et al., J Clin Anesth, 1995. 7(5): p. 359-66). General anesthesia itself, as well as wide surgical fields often used in procedures, produces a rapid decline in the patient's core body temperature (see, e.g., Sessler, D. I., N Engl J Med, 1997. 336(24): p. 1730-7). Intra/perioperative hypothermia increases surgical infections, promotes poor wound healing, leads to cardiovascular stress and increases overall morbidity and mortality associated with surgeries (see, e.g., Sessler, D. I., N Engl J Med, 1997. 336(24): p. 1730-7). Maintenance of perioperative normothermia currently relies on physical means (e.g., forced-air warming blanket, heated intravenous solutions) but these are inadequate in many surgeries (see, e.g., Butwick, A. J., et al., Anesth Analg, 2007. 105(5): p. 1413-9, table of contents; Lin, E. P., K. Smith, and R. D. Valley, Paediatr Anaesth, 2008. 18(7): p. 642-4; Leben, J. and M. Tryba, AnnN Y Acad Sci, 1997. 813: p. 807-11; Brandes, I. F., et al., J Cardiothorac Surg, 2011. 6: p. 117). In fact, turbulent airflow from forced air increases postsurgical infections and poor temperature control can lead to burns (see, e.g., Chung, K., et al., Korean J Anesthesiol, 2012. 62(4): p. 391-2; McGovern, P. D., et al., J Bone Joint Surg Br, 2011. 93(11): p. 1537-44; Baker, N., et al., J Hosp Infect, 2002. 51(2): p. 153-4). The problem of intraoperative hypothermia is particularly severe in neonates and infants who have larger body surface area per body weight and perhaps underdeveloped thermoregulatory mechanisms (see, e.g., Sessler, D. I., Paediatr Anaesth, 2013. 23(6): p. 467-8).

Poor postsurgical pain control results in increased suffering, diminished function, hospital related complications including infections, cardiovascular issues and bleeding, all leading to longer in-hospital stays (see, e.g., Rathmell, J. P., et al., Reg Anesth Pain Med, 2006. 31(4 Suppl 1): p. 1-42; Thomas, T., et al., Pain, 1998. 75(2-3): p. 177-85). Moreover, a strong link exists between acute postsurgical pain intensity and the risk of development of chronic pain (see, e.g., Kehlet, H., T. S. Jensen, and C. J. Woolf, Lancet, 2006. 367(9522): p. 1618-25). Current management of postoperative pain relies primarily on opioids and nonsteroidal anti-inflammatory drugs (NSAIDs). Excessive opioid use in the perioperative phase is associated with increased neurological and respiratory morbidities (see, e.g., Kehlet, H. and K. Holte, Br J Anaesth, 2001. 87(1): p. 62-72). NSAIDs cause increased bleeding, and negatively affect bone healing and kidney function (see, e.g., Souter, A. J., et al., Anesth Analg, 1994. 79(6): p. 1178-90). Multiple anesthetic techniques and drugs have been evaluated as candidates for preemptive analgesics with the hopes of opioid-sparing effect in the postoperative period (see, e.g., Woolf, C. J. and M. S. Chong, Anesth Analg, 1993. 77(2): p. 362-79). Although effective, techniques such as regional anesthesia cannot be used all types of surgeries and drugs such as ketamine and lidocaine have dose limiting side effects (see, e.g., Woolf, C. J. and M. S. Chong, Anesth Analg, 1993. 77(2): p. 362-79). Moreover, regional anesthesia itself can paradoxically contribute to intraoperative hypothermia (see, e.g., Frank et al, Anesthesiology 1992 August 77(2) 252-7; Matsukawa et al, Anesthesiology 1995 November 83(5) 961-7). A drug that can be safely used in the perianesthesia period and also demonstrate preemptive analgesia with opioid-sparing effects could be of exceptional use for an anesthesiologist.

A pharmacological treatment to prevent perioperative hypothermia that may also act as a preemptive analgesic without compromising the cardio/respiratory and neurological status of a patient would be a "silver bullet" for surgeons and for anesthesiologists. A single drug directed toward a molecular target that plays a critical role in both temperature regulation and pain control could revolutionize perioperative care for patients. The present invention addresses and provides a solution for this need. Indeed, the present invention provides compositions and methods for treating and preventing anesthesia-induced hypothermia through use of effective amounts of transient receptor potential channel vanilloid-1 (TRPV1) inhibitors.

TRPV1 is an ion channel expressed predominantly in pain sensing neurons (see, e.g., Cavanaugh, D. J., et al., J Neurosci, 2011. 31(13): p. 5067-77). This channel is a sensor for noxious heat and for increased body temperature (see, e.g., Gavva, N. R., Trends Pharmacol Sci, 2008. 29(11): p. 550-7; Romanovsky A A, et al., Pharmacol Rev 61: 228-261, 2009). TRPV1 agonists produce pain and hypothermia. TRPV1 antagonists have been shown to be devoid of serious cardiovascular and respiratory side effects in humans (see, e.g., Chizh, B. A., et al., Pain, 2007. 132(1-2): p. 132-41) making them ideally suited for their use in the perioperative period. While TRPV1 antagonists elicit analgesia, such TRPV1 antagonists may elicit hyperthermia (see, e.g., Gavva, N. R., Trends Pharmacol Sci, 2008. 29(11): p. 550-7). Indeed, TRPV1 antagonists have not been advanced further in clinical studies because of this side effect (see, e.g., Wong, G. Y. and N. R. Gavva, Brain Res Rev, 2009. 60(1): p. 267-77).

Despite such side effects associated with certain TRPV1 antagonists, experiments conducted during the course of developing embodiments for the present invention determined that regardless of whether the antagonists had the ability to produce hyperthermia in unanesthetized rats, all the tested TRPV1 antagonists demonstrated anti-hypothermia activity under anesthesia. For example, such experiments demonstrated that while the TRPV1 antagonist capsazepine is unable to cause hyperthermia in non-anesthetized rats, it is able to prevent anesthesia-induced hypothermia (see, Example V). This observation indicated that the ability or inability of a TRPV1 antagonist to inhibit hypothermia in non-anesthetized subjects is unrelated to its ability to reverse hypothermia in anesthetized rats. Moreover, the same drugs that cause hyperthermia in unanesthetized animals do not do so even when the animals recover from anesthesia. Additional experiments further investigated this unique and unexpected "anesthesia-specific" effect for TRPV1 antagonists. Indeed, such experiments demonstrated TRPV1 antagonists have an anti-hypothermic effect that is highly advantageous in a perioperative setting to inhibit and/or counterbalance anesthesia-induced hypothermia.

As such, the present invention addresses the need for improved methods for preventing and treating anesthesia-induced hypothermia.

Moreover, experiments conducted herein demonstrated antagonism of TRPV1 before the surgical insult reduces nociceptor sensitization and results in preemptive analgesia. Indeed, such experiments demonstrated that TRPV1 antagonists reversed anesthesia-induced hypothermia without causing hyperthermia when anesthesia wears off. Moreover, it was shown that a single dose of a TRPV1 antagonist given at anesthesia induction has preemptive analgesic effect 24 hours post surgery.

As such, the present invention addresses the need for improved methods for preventing and treating postsurgical associated hyperalgesia.

SUMMARY OF THE INVENTION

In certain embodiments, the present invention provides compositions and methods for treating, ameliorating, and preventing anesthesia-induced hypothermia in a mammalian subject comprising administering to the subject an effective amount of an agent capable of preventing and/or diminishing anesthesia-induced hypothermia (e.g., an ion channel TRPV1 inhibitor).

In some embodiments, the subject is a human being or a veterinary animal about to undergo a treatment involving anesthesia. In some embodiments, the subject is a human being or a veterinary animal being treated with anesthesia. In some embodiments, the subject is a human being or a veterinary animal at risk for developing anesthesia-induced hypothermia. In some embodiments, the subject is a human being or a veterinary animal experiencing anesthesia-induced hypothermia.

The compositions and methods are not limited to a particular type of agent capable of preventing and/or diminishing anesthesia-induced hypothermia. In some embodiments, such an agent is capable of inhibiting TRPV1 activity and/or expression. Indeed, any suitable TRPV1 inhibitor or combination of inhibitors may be used in the methods and compositions herein (e.g., for purposes of inhibiting, preventing and/or treating anesthesia associated hypothermia).

For example, a subject may be treated with a TRPV1 selective inhibitor and a nonselective TRPV1 inhibitor. In some embodiments, the TRPV1 inhibitor is AMG 517 (see, e.g., Gavva, N R, et al., J. Pharmacol Exp Ther, 2007, 323(1), 128-137). In some embodiments, the TRPV1 inhibitor is civamide (zucapsaicin), ABT-102, GRC-6211, AZD1386, SB-705498, NGD 8243/MK-2295, JTS-653, JYL1421, JNJ 17203212, SAR-115740, KJM429, or capsazepine. Additional examples of TRPV1 inhibitors include, but are not limited to, N-(4-tertiarybutylphenyl)-4-(3-chloropyridin-2-yl)-tetrahydropyrazine-1 (2H)-carboxamide; N-(3-Methoxyphenyl)-4-chlorocinnamide; 1-Isoquinolin-5-yl-3-(4-trifluoromethyl-benzyl)-urea; (2E)-N-(2,3-Dihydro-1,4-benzodioxin-6-yl)-3-[4-(1,1-dimethylethyl)phenyl]-2-propenamide; 2-Acetylamino-4-[6'-(4-trifluoromethylphenyl)-pyrimidin-4'-yl-oxy]-benzothiazole; N-(2-bromophenyl)-N'-[((R)-1-(5-trifluoromethyl-2-pyridyl)pyrrolidin-3-yl)]urea; N-(2-bromophenyl)-N'-{2-[ethyl(3-methylphenyl)amino]ethyl}urea; (R)-(5-tert-butyl-2,3-dihydro-1H-inden-1-yl)-3-(1H-indazol-4-yl)-urea; N-(Isoquinolin-5-yl)-N'-[spiro-(cyclobutane-1,2'-(3',4'-dihydro-benzopyran-4'-yl))]urea; (2R)-4-(3-chloro-2-pyridinyl)-2-methyl-N-[4-(trifluoromethyl)phenyl]-1-piperazinecarboxamide; 4-(4'-Trifluoromethyl-anilino)-7-(3'-trifluoromethyl-pyridin-2-yl)-quinazoline; N-[2-(4-chlorophenyl)ethyl]-1,3,4,5-tetrahydro-7,8-dihydroxy-2H-2-benzazepine-2-carbothioamide; (5R*,8R*,6E,9E)-5,8-Dimethyl-4-methylenetetradeca-6,9-dienoic acid; 1-(3-Fluorobenzyl)-2-(N-(1,2-dimethyl-1,3-isoindazol-5-yl)-acetamido)-{pyridine-[3,4-b]-pyrrole}; N-(4-chlorobenzyl)-N'-(1-methyl-1H-indazol-4-yl)urea; N-(4-tert-butylbenzyl)-N'-(1-methyl-1H-indazol-4-yl)urea; N-(3-fluoro-4-(trifluoromethyl)benzyl)-N'-(1-methyl-1H-indazol-4-yl)-urea; N-(4-fluoro-3-(trifluoromethyl)benzyl)-N'-(1-methyl-1H-indazol-4-yl)-urea; N-(3,4-dichlorobenzyl)-N'-(1-methyl-1H-indazol-4-yl)urea; N-(2,4-dichlorobenzyl)-N'-(1-methyl-1H-indazol-4-yl)urea; N-(4-ethylbenzyl)-N'-(1-methyl-1H-indazol-4-yl)urea; N-(2-chlorobenzyl)-N'-(1-methyl-1H-indazol-4-yl)urea; N-(4-fluorobenzyl)-N'-(1-methyl-1H-indazol-4-yl)urea; N-(2-fluorobenzyl)-N'-(1-methyl-1H-indazol-4-yl)urea; N-[1-(bromophenyl)ethyl-N'-(1-methyl-1H-Indazol-4-yl)urea; N-(1-methyl-1H-indazol-4-yl)-N'-{4-[(trifluoromethyl)thio]benzyl}urea; 1-(2,3-dichlorophenyl)-3-[2-(N-ethyl-3-methylanilino)ethyl]urea; 1-[2-(N-ethyl-3-methylanilino)ethyl]-3-naphthalen-1-ylurea; 1-(4-bromophenyl)-3-[2-(N-ethyl-3-methylanilino)ethyl]urea; 1-(3-bromophenyl)-3-[2-(N-ethyl-3-methylanilino)ethyl]urea; 1-(chlorophenyl)-3-[2-(N-ethyl-3-methylanilino)ethyl]urea; 1-[2-(N-ethyl-3-methylanilino)ethyl]-3-(2-fluorophenyl)urea; 1-[2-{N-ethyl-3- methylanilino)ethyl]-3-(2-methylphenyl)urea; 1-[2-(N-ethyl-3-methylanilino)ethyl]-3-phenylurea; 2-[(2-bromophenyl)carbamoylamino]ethyl-ethylmethyl-(3-methylphenyl)azanium iodide; 1-(2-bromophenyl)-3-[2-(N-ethyl-3-fluoro-4-methylanilino)ethyl]urea; 1-(2-bromophenyl)-3-[2-(N-ethyl-3,4-difluoroanilino)ethyl]urea; 1-(2-bromophenyl)-3-[2-(N-ethyl-3-fluoroanilino)ethyl] urea; 1-(2-bromophenyl)-3-[2-(N-ethyl-4-methylanilino) ethyl]urea; 1-(2-bromophenyl)-3-[2-(N-ethyl-2-methylanilino)ethyl]urea; 1-(2-bromophenyl)-3-[2-(N-ethylanilino)ethyl]urea; N-[2-[(2-bromophenyl) carbamoylamino]ethyl]-N-(3-methylphenyl)acetamide; 1-[2-{N-benzyl-3-methylanilino)ethyl]-3-(2-bromophenyl) urea; 1-(2-bromophenyl)-3-[2-(2,3-dimethylanilino)ethyl] urea; 1-(2-bromophenyl)-3-[2-(3-methylanilino)ethyl]urea; 1-(2,5-dichlorophenyl)-3-[2-(N-ethyl-3-methylanilino) ethyl]urea; 4-fluoro-4-(3-methylpyridin-2-yl)-N-[4-trifluoromethylphenyl]piperidine-1-carboxamide; 4-fluoro-4(pyridin-2-yl)N-[4-trifluoromethylphenyl]piperidine-1-carboxamide; 4-fluoro-4(pyridine-2-yl)N-[4-trifluoromethylbenzyl]piperidine-1-carboxamide; 2-{4-fluoro-1-[4-trifluoromethylbenzoyl]piperidin-4-yl}pyridine; 2-(4-fluoro-1-{[4-trifluoromethylphenyl]acetyl}piperidin-4-yl)pyridine; 2-(4-fluoro-1-{3-[4-trifluoromethylphenyl] propanoyl}piperidin-4-yl)pyridine; 4-fluoro-4-(1-methyl-1H-imidazol-2-yl)-N-[4-trifluoromethylphenyl]piperidine-1-carboxamide; 4-methoxy-4-pyridin-2-yl-N-[4-trifluoromethylphenyl]piperidine-1-carboxamide; 4-methoxy-4-pyridin-2-yl-N-[4-trifluoromethylbenzyl]piperidine-1-carboxamide; 4-fluoro-N-(4-isopropylphenyl)-4-(3-methylpyridin-2-yl)piperidine-1-carboxamide; 4-fluoro-4-(3-methylpyridin-2-yl)-N-{4-[1,2,2,2-tetrafluoro-1-trifluoromethylethyl]phenyl}piperidine-1-carboxamide; N-(4-Tert-butylphenyl)-4-fluoro-4-(3-methylpyridin-2-yl) piperidine-1-carboxamide; 4-fluoro-4-(3-methylpyridin-2-yl)-N-[4-(pentafluoro-lambda(sup 6)-sulfanyl)phenyl]piperidine-1-carboxamide; N-(4-Butylphenyl)-4-fluoro-4-(3-methylpyridin-2-yl)piperidine-1-carboxamide; N-(4-Benzylphenyl)-4-fluoro-4-(3-methylpyridin-2-yl) piperidine-1-carboxamide; N-biphenyl-4-yl-4-fluoro-4-(3-methylpyridin-2-yl)piperidine-1-carboxamide; 4-fluoro-4-(3-methylpyridin-2-yl)-N-[5-trifluoromethylpyridin-2-yl] piperidine-1-carboxamide; 4-(3-chloropyridin-2-yl)-4-fluoro-N-[4-trifluoromethylphenyl]piperidine-1-carboxamide; 4-fluoro-4-(3-fluoropyridin-2-yl)-N-[4-trifluoromethylphenyl]piperidine-1-carboxamide; 4-fluoro-4-(3-methoxypyridin-2-yl)-N-[4-trifluoromethylphenyl] piperidine-1-carboxamide; 4-fluoro-4-(3-methylpyridin-2-yl)-N-[4-trifluoromethylphenyl]piperidine-1-carbothioamide; N'-cyano-4-fluoro-4-(3-methylpyridin-2-yl)-N-[4-trifluoromethylphenyl]piperidine-1-carboximidamide; 4-fluoro-4-(3-methylpyridin-2-yl)-N'-(1-phenylpiperidin-4-yl)-N-[4-trifluoromethylphenyl] piperidine-1-carboximidamide; 4-fluoro-4-phenyl-N-[4-trifluoromethylphenyl]piperidine-1-carboxamide; (+/−)-(syn)-4-fluoro-2-methyl-4-(3-methylpyridin-2-yl)-N-[4-trifluoromethylphenyl]piperidine-1-carboxamide; 4-(fluoromethyl)-4-pyridin-2-yl-N-[4-trifluoromethylphenyl]piperidine-1-carboxamide; syn- and anti-3-fluoro-3-pyridin-2-yl-N-[4-trifluoromethylphenyl]-8-azabicyclo [3.2.1]octane-8-carboxamide; 3-fluoro-3-pyridin-2-yl-N-[4-trifluoromethylphenyl]-8-azabicyclo[3.2.1]octane-8-carboxamide; 4-fluoro-4-pyrimidin-2-yl-N-[4-trifluoromethylphenyl]piperidine-1-carboxamide; 4-fluoro-4-(3-phenylpropyl)-N-[4-trifluoromethylphenyl]piperidine-1-carboxamide; 2-[4-fluoro-4-(3-methylpyridin-2-yl) piperidin-1-yl]-6-trifluoromethyl-1H-benzimidazole; 2-(4-fluoro-4-pyridin-2-ylpiperidin-1-yl)-6-(trifluoromethyl)-1H-benzimidazole; 4-fluoro-N-[4-trifluoromethyiphenyl]-4-[3-trifluoromethylpyridin-2-yl]piperidine-1-carboxamide; 4-fluoro-N-(4-methylphenyl)-4-(3-methylpyridin-2-yl)piperidine-1-carboxamide; N-(4-ethylphenyl)-4-fluoro-4-(3-methylpyridin-2-yl)piperidine-1-carboxamide; N-(4-chlorophenyl)-4-fluoro-4-(3-methylpyridin-2-yl)piperidine-1-carboxamide; 4-fluoro-4-(3-methylpyridin-2-yl)-N-[4-trifluoromethoxyphenyl]piperidine-1-carboxamide; N-(4-cyanophenyl)-4-fluoro-4-(3-methylpyridin-2-yl)piperidine-1-carboxamide; N-[4-dimethylaminophenyl]-4-fluoro-4-(3-methylpyridin-2-yl)piperidine-1-carboxamide; 1-(2-(3,3-dimethylbutyl)-4-(trifluoromethyl)benzyl)-3-(1-methyl-1H-indazo-1-4-yl)urea; N-acetyl-1-phenylalanyl-1-leucinamide; and pharmaceutically acceptable salts thereof.

In some embodiments, the TRPV1 antagonist is selected from AMG 517, capsazepine, SB-366791, AMG 9810, and/or ABT-102.

In some embodiments, the TRPV1 inhibitor is administered before, after, or simultaneously with administration of a general anesthesia. Examples of general anesthesia include inhalation anesthetics such as isoflurane, halothane, methoxyflurane and the like; intravenous anesthetics such as sodium thiopental, ketamine, propofol and the like; induction anesthetics used along with inhalation anesthetics; and combinations thereof.

Such agents are not limited to a particular mechanism and/or manner for preventing and/or diminishing anesthesia-induced hypothermia. In some embodiments, the agents are capable of preventing and/or hindering anesthesia related temperature loss. In some embodiments, the agents are capable of increasing the temperature of the subject to counter the anesthesia-induced temperature loss.

In certain embodiments, methods for preventing and/or diminishing postsurgical hyperalgesia in a subject are provided. For example, in some embodiments, such methods comprise administration of a TRPV1 antagonist prior to surgical onset for purposes of preventing and/or diminishing pain (e.g., hyperalgesia) experienced post-surgery. Such methods are not limited to a particular subject. In some embodiments, the subject is a human being or a veterinary animal about to undergo a surgical procedure likely to result in postsurgical hyperalgesia.

Such methods are not limited to a particular TRPV1 antagonist. For example, in some embodiments, the TRPV1 inhibitor is AMG 517 (see, e.g., Gavva, N R, et al., J. Pharmacol Exp Ther, 2007, 323(1), 128-137). In some embodiments, the TRPV1 inhibitor is civamide (zucapsaicin), ABT-102, GRC-6211, AZD1386, SB-705498, NGD 8243/MK-2295, JTS-653, JYL1421, JNJ 17203212, SAR-115740, KJM429, or capsazepine. Additional examples of TRPV1 inhibitors include, but are not limited to, N-(4-tertiarybutylphenyl)-4-(3-chloropyridin-2-yl)-tetrahydropyrazine-1(2H)-carboxamide; N-(3-Methoxyphenyl)-4-chlorocinnamide; 1-Isoquinolin-5-yl-3-(4-trifluoromethylbenzyl)-urea; (2E)-N-(2,3-Dihydro-1,4-benzodioxin-6-yl)-3-[4-(1,1-dimethylethyl)phenyl]-2-propenamide; 2-Acetylamino-4-[6'-(4-trifluoromethylphenyl)-pyrimidin-4'-yl-oxy]-benzothiazole; N-(2-bromophenyl-N'-[((R)-1-(5-trifluoromethyl-2-pyridyl)pyrrolidin-3-yl)]urea; N-(2-bromophenyl)-N'-{2-[ethyl(3-methylphenyl)amino]ethyl}urea; (R)-(5-tert-butyl-2,3-dihydro-1H-inden-1-yl)-3-(1H-indazol-4-yl)-urea; N-(Isoquinolin-5-yl)-N'-[spiro-(cyclobutane-1,2'-(3',4'-dihydro-benzopyran-4'-yl))]urea; (2R)-4-(3-chloro-2-pyridinyl)-2-methyl-N-[4-(trifluoromethyl) phenyl]-1-piperazinecarboxamide; 4-(4'-Trifluoromethylanilino)-7-(3'-trifluoromethyl-pyridin-2-yl)-quinazoline;

N-[2-(4-chlorophenyl)ethyl]-1,3,4,5-tetrahydro-7,8-dihydroxy-2H-2-benzazepine-2-carbothioamide; (5R*,8R*,6E,9E)-5,8-Dimethyl-4-methylenetetradeca-6,9-dienoic acid; 1-(3-Fluorobenzyl)-2-(N-(1,2-dimethyl-1,3-isoindazol-5-yl)-acetamido)-{pyridine-[3,4-b]-pyrrole}; N-(4-chlorobenzyl)-N'-(1-methyl-1H-indazol-4-yl)urea; N-(4-tert-butylbenzyl)-N'-(1-methyl-1H-indazol-4-yl)urea; N-(3-fluoro-4-(trifluoromethyl)benzyl)-N'-(1-methyl-1H-indazol-4-yl)-urea; N-(4-fluoro-3-(trifluoromethyl)benzyl)-N'-(1-methyl-1H-indazol-4-yl)-urea; N-(3,4-dichlorobenzyl)-N'-(1-methyl-1H-indazol-4-yl)urea; N-(2,4-dichlorobenzyl)-N'-(1-methyl-1H-indazol-4-yl)urea; N-(4-ethylbenzyl)-N'-(1-methyl-1H-indazol-4-yl)urea; N-(2-chlorobenzyl)-N'-(1-methyl-1H-indazol-4-yl)urea; N-(4-fluorobenzyl)-N'-(1-methyl-1H-indazol-4-yl)urea; N-(2-fluorobenzyl)-N'-(1-methyl-1H-indazol-4-yl)urea; N-[1-(bromophenyl)ethyl-N'-(1-methyl-1H-Indazol-4-yl)urea; N-(1-methyl-1H-indazol-4-yl)-N'-{4-[(trifluoromethyl)thio]benzyl}urea; 1-(2,3-dichlorophenyl)-3-[2-(N-ethyl-3-methylanilino)ethyl]urea; 1-[2-(N-ethyl-3-methylanilino)ethyl]-3-naphthalen-1-ylurea; 1-(4-bromophenyl)-3-[2-(N-ethyl-3-methylanilino)ethyl]urea; 1-(3-bromophenyl)-3-[2-(N-ethyl-3-methylanilino)ethyl]urea; 1-(chlorophenyl)-3-[2-(N-ethyl-3-methylanilino)ethyl]urea; 1-[2-(N-ethyl-3-methylanilino)ethyl]-3-(2-fluorophenyl)urea; 1-[2-{N-ethyl-3-methylanilino)ethyl]-3-(2-methylphenyl)urea; 1-[2-(N-ethyl-3-methylanilino)ethyl]-3-phenylurea; 2-[(2-bromophenyl)carbamoylamino]ethyl-ethylmethyl-(3-methylphenyl)azanium iodide; 1-(2-bromophenyl)-3-[2-(N-ethyl-3-fluoro-4-methylanilino)ethyl]urea; 1-(2-bromophenyl)-3-[2-(N-ethyl-3,4-difluoroanilino)ethyl]urea; 1-(2-bromophenyl)-3-[2-(N-ethyl-3-fluoroanilino)ethyl]urea; 1-(2-bromophenyl)-3-[2-(N-ethyl-4-methylanilino)ethyl]urea; 1-(2-bromophenyl)-3-[2-(N-ethyl-2-methylanilino)ethyl]urea; 1-(2-bromophenyl)-3-[2-(N-ethylanilino)ethyl]urea; N-[2-[(2-bromophenyl)carbamoylamino]ethyl]-N-(3-methylphenyl)acetamide; 1-[2-{N-benzyl-3-methylanilino)ethyl]-3-(2-bromophenyl)urea; 1-(2-bromophenyl)-3-[2-(2,3-dimethylanilino)ethyl]urea; 1-(2-bromophenyl)-3-[2-(3-methylanilino)ethyl]urea; 1-(2,5-dichlorophenyl)-3-[2-(N-ethyl-3-methylanilino)ethyl]urea; 4-fluoro-4-(3-methylpyridin-2-yl)-N-[4-trifluoromethylphenyl]piperidine-1-carboxamide; 4-fluoro-4(pyridin-2-yl)N-[4-trifluoromethylphenyl]piperidine-1-carboxamide; 4-fluoro-4(pyridine-2-yl)N-[4-trifluoromethylbenzyl]piperidine-1-carboxamide; 2-{4-fluoro-1-[4-trifluoromethylbenzoyl]piperidin-4-yl}pyridine; 2-(4-fluoro-1-{[4-trifluoromethylphenyl]acetyl}piperidin-4-yl)pyridine; 2-(4-fluoro-1-{3-[4-trifluoromethylphenyl]propanoyl}piperidin-4-yl)pyridine; 4-fluoro-4-(1-methyl-1H-imidazol-2-yl)-N-[4-trifluoromethylphenyl]piperidine-1-carboxamide; 4-methoxy-4-pyridin-2-yl-N-[4-trifluoromethylphenyl]piperidine-1-carboxamide; 4-methoxy-4-pyridin-2-yl-N-[4-trifluoromethylbenzyl]piperidine-1-carboxamide; 4-fluoro-N-(4-isopropylphenyl)-4-(3-methylpyridin-2-yl)piperidine-1-carboxamide; 4-fluoro-4-(3-methylpyridin-2-yl)-N-{4-[1,2,2,2-tetrafluoro-1-trifluoromethylethyl]phenyl}piperidine-1-carboxamide; N-(4-Tert-butylphenyl)-4-fluoro-4-(3-methylpyridin-2-yl)piperidine-1-carboxamide; 4-fluoro-4-(3-methylpyridin-2-yl)-N-[4-(pentafluoro-lambda(sup 6)-sulfanyl)phenyl]piperidine-1-carboxamide; N-(4-Butylphenyl)-4-fluoro-4-(3-methylpyridin-2-yl)piperidine-1-carboxamide; N-(4-Benzylphenyl)-4-fluoro-4-(3-methylpyridin-2-yl)piperidine-1-carboxamide; N-biphenyl-4-yl-4-fluoro-4-(3-methylpyridin-2-yl)piperidine-1-carboxamide; 4-fluoro-4-(3-methylpyridin-2-yl)-N-[5-trifluoromethylpyridin-2-yl] piperidine-1-carboxamide; 4-(3-chloropyridin-2-yl)-4-fluoro-N-[4-trifluoromethylphenyl]piperidine-1-carboxamide; 4-fluoro-4-(3-fluoropyridin-2-yl)-N-[4-trifluoromethylphenyl]piperidine-1-carboxamide; 4-fluoro-4-(3-methoxypyridin-2-yl)-N-[4-trifluoromethylphenyl]piperidine-1-carboxamide; 4-fluoro-4-(3-methylpyridin-2-yl)-N-[4-trifluoromethylphenyl]piperidine-1-carbothioamide; N'-cyano-4-fluoro-4-(3-methylpyridin-2-yl)-N-[4-trifluoromethylphenyl]piperidine-1-carboximidamide; 4-fluoro-4-(3-methylpyridin-2-yl)-N'-(1-phenylpiperidin-4-yl)-N-[4-trifluoromethylphenyl]piperidine-1-carboximidamide; 4-fluoro-4-phenyl-N-[4-trifluoromethylphenyl]piperidine-1-carboxamide; (+/−)-(syn)-4-fluoro-2-methyl-4-(3-methylpyridin-2-yl)-N-[4-trifluoromethylphenyl]piperidine-1-carboxamide; 4-(fluoromethyl)-4-pyridin-2-yl-N-[4-trifluoromethylphenyl]piperidine-1-carboxamide; syn- and anti-3-fluoro-3-pyridin-2-yl-N-[4-trifluoromethylphenyl]-8-azabicyclo[3.2.1]octane-8-carboxamide; 3-fluoro-3-pyridin-2-yl-N-[4-trifluoromethylphenyl]-8-azabicyclo[3.2.1]octane-8-carboxamide; 4-fluoro-4-pyrimidin-2-yl-N-[4-trifluoromethylphenyl]piperidine-1-carboxamide; 4-fluoro-4-(3-phenylpropyl)-N-[4-trifluoromethylphenyl]piperidine-1-carboxamide; 2-[4-fluoro-4-(3-methylpyridin-2-yl)piperidin-1-yl]-6-trifluoromethyl-1H-benzimidazole; 2-(4-fluoro-4-pyridin-2-ylpiperidin-1-yl)-6-(trifluoromethyl)-1H-benzimidazole; 4-fluoro-N-[4-trifluoromethyiphenyl]-4-[3-trifluoromethylpyridin-2-yl]piperidine-1-carboxamide; 4-fluoro-N-(4-methylphenyl)-4-(3-methylpyridin-2-yl)piperidine-1-carboxamide; N-(4-ethylphenyl)-4-fluoro-4-(3-methylpyridin-2-yl)piperidine-1-carboxamide; N-(4-chlorophenyl)-4-fluoro-4-(3-methylpyridin-2-yl)piperidine-1-carboxamide; 4-fluoro-4-(3-methylpyridin-2-yl)-N-[4-trifluoromethoxyphenyl]piperidine-1-carboxamide; N-(4-cyanophenyl)-4-fluoro-4-(3-methylpyridin-2-yl)piperidine-1-carboxamide; N-[4-dimethylaminophenyl]-4-fluoro-4-(3-methylpyridin-2-yl)piperidine-1-carboxamide; 1-(2-(3,3-dimethylbutyl)-4-(trifluoromethyl)benzyl)-3-(1-methyl-1H-indazo-1-4-yl)urea; N-acetyl-1-phenylalanyl-1-leucinamide; and pharmaceutically acceptable salts thereof.

In some embodiments, the TRPV1 antagonist is selected from AMG 517, capsazepine, SB-366791, AMG 9810, and/or ABT-102.

Such methods are not limited to a specific administration schedule for the composition in relation to surgical onset. In some embodiments, the composition is administered less than 10 minutes prior to surgical onset. In some embodiments, the composition is administered less than 5 minutes prior to surgical onset. In some embodiments, the composition is administered less than 2 minutes prior to surgical onset. In some embodiments, the composition is administered less than 1 minute prior to surgical onset. In some embodiments, the composition is administered simultaneous with surgical onset.

In some embodiments, the composition is a pharmaceutical composition.

In certain embodiments, the present invention provides compositions comprising an agent capable of preventing and/or diminishing anesthesia-induced hypothermia in a mammalian subject (e.g., a human subject), wherein the agent is an ion channel TRPV1 inhibitor. Such compositions are not limited to a particular type or kind of TRPV1 inhibitor (e.g., any TRPV1 inhibitor and/or antagonist as described herein). In some embodiments, the TRPV1 inhibitor is selected from AMG 517, capsazepine, SB-366791, AMG 9810, and/or ABT-102. In some embodiments, the composition is a pharmaceutical composition.

In certain embodiments, the present invention provides kits comprising one or more compositions comprising an agent capable of preventing and/or diminishing anesthesia-induced hypothermia in a mammalian subject (e.g., a human subject), wherein the agent is an ion channel TRPV1 inhibitor, and one or more of an inhalation anesthetic and/or an intravenous anesthetic. In some embodiments, the inhalation anesthetic is selected from isoflurane, sevoflurane, desflurane, halothane, methoxyflurane and the like. In some embodiments, the intravenous anesthetic is selected from sodium thiopental, ketamine, propofol and the like. In some embodiments, the TRPV1 inhibitor is selected from AMG 517, capsazepine, SB-366791, AMG 9810, and/or ABT-102. In some embodiments, the composition is a pharmaceutical composition.

DETAILED DESCRIPTION OF THE INVENTION

Figure 1:
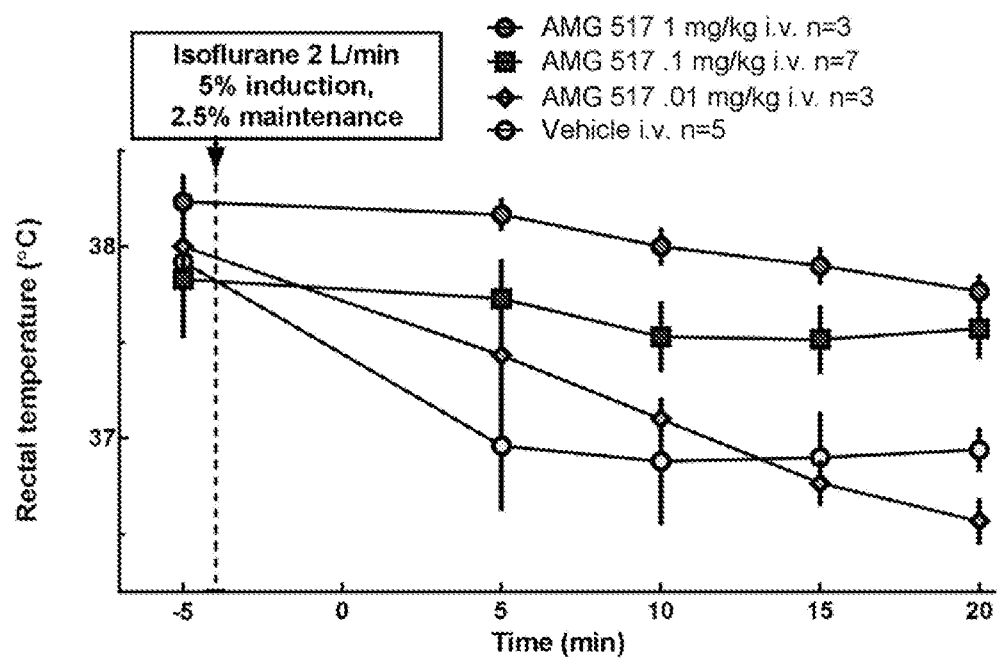
FIG. 1 shows the effect of TRPV1 antagonism (e.g., AMG 517) on anesthesia-induced hypothermia. The effect of varying dosage levels of AMG 517 (10 µg, 100 µg, 1000 µg) and control (vehicle) on rectally measured temperature after induction of anesthesia with isoflurane as a function of time was compared.

In patients undergoing general anesthesia for various surgeries, core body temperature begins to drop as soon as anesthesia is induced (see, e.g., Sessler, D. I., N Engl J Med, 1997. 336(24): p. 1730-7). Multiple factors contribute to this drop and principal among them are anesthetic-induced blood flow redistribution and a centrally-mediated decrease in threshold body temperature for shivering, plus evaporative loss from large surface areas exposed during open surgical fields (see, e.g., Sessler, D. I., N Engl J Med, 1997. 336(24): p. 1730-7). Hypothermia-induced during the surgery has a substantial deleterious effect on normal physiology of the patient. Apart from altering drug metabolism, hypothermia alters function of coagulation factors leading to increased bleeding, use of various blood products and all the risks associated with them. Secondly, hypothermia decreases immune function resulting in increased incidence of post-operative infections (see, e.g., Sessler, D. I., N Engl J Med, 1997. 336(24): p. 1730-7). Finally, when the patient is emerging from anesthesia, hypothermia leads to increased shivering. Shivering causes high cardiovascular stress that can precipitate cardiac complications in susceptible individuals (see, e.g., Sessler, D. I., N Engl J Med, 1997. 336(24): p. 1730-7; Lenhardt, R., et al., Anesthesiology, 1997. 87(6): p. 1318-23; Leben, J. and M. Tryba, AnnN Y Acad Sci, 1997. 813: p. 807-11). In neonates, normal cold defense response is underdeveloped and the neonate more relies on non-shivering thermogenesis (see, e.g., Sessler, D. I., Paediatr Anaesth, 2013. 23(6): p. 467-8). Anesthesia-induced hypothermia in neonates is more pronounced and can lead to devastating consequences such as cardiac arrhythmia and coagulopathy (see, e.g., Tander, B., et al., Paediatr Anaesth, 2005. 15(7): p. 574-9).

The prevention of hypothermia is one of the critical tasks of an anesthesiologist and perioperative staff. Given the importance of temperature homeostasis, continuous monitoring of core body temperature is mandatory under general anesthesia and appropriate temperature constitutes one of the critical components of successful post anesthesia recovery (see, e.g., ASA, STANDARDS FOR BASIC ANESTHETIC MONITORING. 2011). Currently, the only modes available to prevent/treat hypothermia are physical ways of warming the patient, i.e. forced air or circulating water warming blanket and warm intravenous fluids. These modalities are modestly effective at best and are simply inadequate in many cases (see, e.g., Butwick, A. J., et al., Anesth Analg, 2007. 105(5): p. 1413-9, table of contents; Lin, E. P., et al., Paediatr Anaesth, 2008. 18(7): p. 642-4; Leben, J. and M. Tryba, AnnN Y Acad Sci, 1997. 813: p. 807-11). Moreover, forced air warming blanket increases the probability of bacterial contamination of surgical wounds and burn injury to patients, resulting in prolonged hospital stays (see, e.g., Chung, K., et al., Korean J Anesthesiol, 2012. 62(4): p. 391-2; McGovern, P. D., et al., J Bone Joint Surg Br, 2011. 93(11): p. 1537-44; Baker, N., D. King, and E. G. Smith, J Hosp Infect, 2002. 51(2): p. 153-4). A medication that directly modulates the thermoregulatory system has the potential to be more effective than physical ways of warming the patient.

The ion channel TRPV1 was discovered nearly 15 years ago as a principal thermosensor expressed on peripheral pain sensing neurons (see, e.g., Julius, D., Annu Rev Cell Dev Biol, 2013. 29: p. 355-84). When TRPV1 antagonists were undergoing clinical trials in healthy volunteers and for potential analgesic benefit in outpatient populations, an untoward side effect of fever was noted in many subjects (see, e.g., Gavva, N. R., Trends Pharmacol Sci, 2008. 29(11): p. 550-7). These findings resulted in a detailed scientific enquiry into the role of TRPV1 in thermoregulation. According to some studies, TRPV1 is expressed in the anatomical structures involved in body temperature regulation i.e. hypothalamus, vascular smooth muscle and peripheral sensory terminals but not in other parts of the brain (see, e.g., Cavanaugh, D. J., et al., J Neurosci, 2011. 31(13): p. 5067-77). Antagonism of TRPV1 results in hyperthermia that is brought about by peripheral vasoconstriction and increased thermogenesis (see, e.g., Steiner A A, et al., J Neurosci 27: 7459-7468, 2007; Gavva N R, et al., Pain 136: 202-210, 2008). Importantly, a number of TRPV1 antagonists have already undergone safety trials in humans and are devoid of serious cardiorespiratory and neurological side effects making them an attractive option in the perioperative setting (see, e.g., Chizh, B. A., et al., Pain, 2007. 132(1-2): p. 132-41).

Effective pain control in the postsurgical period is the second most important criteria of successful anesthetic care. It has been reported that almost 50-70% of patients undergoing surgery report moderate-to-severe pain after surgery, demonstrating the inadequacy of current treatments (see, e.g., Brennan, T. J., et al., Pain, 2011. 152(3 Suppl): p. S33-40). Apart from obvious patient discomfort, poor pain control in the immediate postoperative period can result in increased cardiovascular stress and morbidities, bleeding from surgical sites, increased pulmonary complications and protracted recovery period (see, e.g., Brennan, T. J., et al., Pain, 2011. 152(3 Suppl): p. S33-40). Moreover, inadequate acute pain control can lead to development of chronic pain conditions that place a tremendous burden on patients and society in general (see, e.g., Kehlet, H., T. S. Jensen, and C. J. Woolf, Lancet, 2006. 367(9522): p. 1618-25). Multiple medications are used to control postoperative pain and they include opioids, nonsteroidal anti-inflammatory drugs, ketamine, and clonidine among others. Opioids and NSAIDs are the most commonly used analgesics for peri- and postoperative pain. In many surgical situations, NSAIDs are either contraindicated or used with extreme caution due to their deleterious effect on postoperative bleeding, kidney function and bone healing (see, e.g., Souter, A. J., B. Fredman, and P. F. White, Anesth Analg, 1994. 79(6): p. 1178-90). Opioids on the other hand can cause respiratory depression, sedation, increased nausea/vomiting and ileus resulting in delayed recovery (see, e.g., White, P. F., Anesth Analg, 2005. 101(5 Suppl): p. S5-22). A unique aspect of peri- and postsurgical pain is that the timing of tissue injury (i.e. surgery) is known ahead of time, giving an opportunity to decrease nociceptor sensitization before the injury such that post-injury pain is reduced and requires shorter-term analgesic therapy (preemptive analgesia). Extensive research in the field of preemptive analgesia has resulted in the development of regional anesthetic techniques and infusions of drugs such as ketamine and lidocaine as strategies to reduce the need for postoperative opioids (see, e.g., Woolf, C. J. and M. S. Chong, Anesth Analg, 1993. 77(2): p. 362-79). However, regional anesthetic techniques are not suitable in a variety of surgeries (e.g. cardiac) and both ketamine and lidocaine have serious dose-limiting side effects (e.g. cardiovascular) (see, e.g., Woolf, C. J. and M. S. Chong, Anesth Analg, 1993. 77(2): p. 362-79). Moreover, regional anesthesia itself can contribute to intraoperative hypothermia (Frank et al, Anesthesiology 1992 August 77(2) 252-7; Matsukawa et al, Anesthesiology 1995 November 83(5) 961-7). It is important to note that just because certain drug is an analgesic, it does not mean it would have preemptive analgesic effects. For example, some opioids such as remifentanil, given preemptively, may actually produce postoperative opioid-induced hyperalgesia which requires higher doses of opioids or other analgesics to control in the postoperative setting (Guignard et al, Anesthesiology, 2000 August 93(2) 409-417). Any drug that can reduce the reliance on opioids and NSAIDs without affecting cardio/respiratory and neurological status of a postsurgical patient will result in faster postoperative recovery that has implications for both patient satisfaction and cost of healthcare.

The pathophysiology of postsurgical pain involves multiple complex mechanisms that begin with the tissue injury. Surgical insult in a tissue results in an inflammatory cascade generating a variety of mediators such as arachidonic and linoleic acid metabolites, tumor necrosis factor-alpha, serotonin, interleukins amongst others (see, e.g., Brennan, T. J., Pain, 2011. 152(3 Suppl): p. S33-40). Some of these mediators directly activate or sensitize receptors expressed on pain sensing sensory terminals. Continuous activation/sensitization of the pain sensing neurons (nociceptors) leads to changes in the peripheral and central nervous system such that sensory neurons innervating the injured area start responding even to non-painful stimuli (allodynia) and respond excessively to painful stimuli (hyperalgesia) (see, e.g., Brennan, T. J., Pain, 2011. 152(3 Suppl): p. S33-40). These phenomena are also known as central and peripheral sensitization (see, e.g., Woolf, C. J., Pain, 2011. 152(3 Suppl): p. S2-15). Multiple studies have demonstrated that one of the receptors expressed on the nociceptors that plays a critical role in generation and maintenance of sensitized states such as postsurgical pain state is TRPV1 (see, e.g., Barabas, M. E. and C. L. Stucky, Mol Pain, 2013. 9: p. 9; Wu, C., et al., Anesthesiology, 2008. 108(6): p. 1100-8; Pogatzki-Zahn, E. M., et al., Pain, 2005. 115(3): p. 296-307).

TRPV1 was originally discovered as a primary receptor for detecting noxious heat. TRPV1 is activated by physical stimuli such as noxious temperature and low pH (see, e.g., Julius, D., Annu Rev Cell Dev Biol, 2013. 29: p. 355-84). Moreover, exogenous substances such as capsaicin (a chemical in the hot chili pepper) and endogenous substances such as anandamide and linoleic acid metabolites act as an agonist of TRPV1 (see, e.g., Patwardhan, A. M., et al., J Clin Invest, 2010. 120(5): p. 1617-26). Inflammatory mediators such as prostaglandins, serotonin, tumor necrosis factor- and chemokines can sensitize the channel lowering its threshold for activation to body temperature (see, e.g., Julius, D., Annu Rev Cell Dev Biol, 2013. 29: p. 355-84). TRPV1 is expressed in a distinct population of pain sensing neurons innervating skin and muscles and the activation of the channel at these nerve endings can result in a prolonged state of hypersensitivity (see, e.g., Cavanaugh, D. J., et al., J Neurosci, 2011. 31(13): p. 5067-77; Barabas, M. E. and C. L. Stucky, Mol Pain, 2013. 9: p. 9; Pogatzki-Zahn, E. M., et al., Pain, 2005. 115(3): p. 296-307). Interestingly, cutaneous hypersensitivity is a hallmark feature of postsurgical pain and endogenous activators and sensitizers of TRPV1 such as protons, prostaglandin and other inflammatory mediators are abundant in the surgical wound (see, e.g., Brennan, T. J., Pain, 2011. 152(3 Suppl): p. S33-40). Antagonists of TRPV1 given after the surgical insult can decrease pain in animal models of pain; but are of limited value in most clinical situations due to the side effect of hyperthermia (see, e.g., Wong, G. Y. and N. R. Gavva, Brain Res Rev, 2009. 60(1): p. 267-77). However, no study has evaluated the effect antagonist of TRPV1 given while the patient is under anesthesia. Intraoperative TRPV1 antagonist can potentially reduce TRPV1 activation during and after surgery and hence result in decreased pain, reduced postoperative opioids and faster postsurgical recovery.

Under anesthesia, the spectrum of effectors involved in thermoregulation is different from that under normal conditions. For example, thermoregulatory behaviors (selecting preferred ambient temperature and temperature-appropriate clothes, changing the body pose, etc.) are not available under anesthesia. Shivering (see, e.g., Sessler, et al., Anesthesiology 109: 318-38, 2008) and, for some anesthetics, brown fat thermogenesis (see, e.g., Ohlson K B E, et al., Anesthesiology 98:437-48, 2003) are also inhibited in anesthesia. Hence, if a substance causes hyperthermia in unanesthetized animals by affecting behavior or increasing thermogenesis, it may have no effect on body temperature under anesthesia.

In addition, anesthesia typically causes hypothermia, and effects of many compounds on body temperature are highly sensitive to the basal level of temperature. In other words, if a compound causes a certain change in body temperature under normal conditions, it is impossible to tell in advance what would be the effect of the same compound when it is administered under different thermal conditions. For example, many cyclooxygenase inhibitors decrease body temperature during fever, but do not affect (at the same doses) normal body temperature and, in some conditions, may even cause hyperthermia (see, e.g., Aronoff D M, et al., Prog Brain Res 162: 15-25, 2007). Many compounds (e.g., prostaglandin $E_1$, prostaglandin $E_2$, and cholecystominin-8) cause pronounced hyperthermia at a lower body temperature in rats, but produce a smaller hyperthermic effect or no effect (see, e.g., Szelenyi Z, et al., Brain Res 638: 69-77, 1994) or even hypothermia (see, e.g., Morimoto A, et al., Physiol Behav 50: 249-53, 1991) at a higher body temperature in the same species. Several substances (e.g., platelet-activating factor (see, e.g., Ivanov A I, et al., J Physiol 553: 221-8, 2003) and lipopolysaccharide (see, e.g., Steiner A A, et al., Prog Lipid Res 46: 89-107, 2007) produce hyperthermia in a thermoneutral (normal) environment, but cause deep hypothermia (due to a decrease in thermogenesis (see, e.g., Romanovsky A A, et al., Am J Physiol 270: R693-703, 1996) at just slightly lower than ambient temperatures. Similarly, norepinephrine increases thermogenesis in a warm environment, but decreases thermogenesis in the cold (see, e.g., Zylan K D, Carlisle H J. Pharmacol Biochem Behav 43: 577-82, 1992). Indeed, that fact that TRPV1 antagonists raise body temperature in unanesthetized humans and laboratory animals by 1-2° C. to a range of 38-39° C. or higher does not allow one to predict whether and how they will affect body temperature under anesthesia.

Experiments conducted during the course of developing embodiments for the present invention further investigated the activity of pharmaceutical agents in subjects that are "anesthetized" versus "non-anesthetized." It was determined that while certain TRPV1 antagonists (e.g., AMG517, MK-2295, AZD1386, AMG 9810, and ABT 102) are able to cause hyperthermia in non-anesthetized rats and humans, other TRPV1 antagonists (e.g., capsazepine SB366791, and A-1165442) were unable to cause hyperthermia in non-anesthetized rats (see, Voight, et al., J. Med. Chem. 2014 Sep. 11:57(17) 7412-24; Garami, et al., 2010 J. Neurosci. 30(4): 1435-1440). This observation indicated that the ability or inability of a TRPV1 antagonist to inhibit hypothermia in non-anesthetized subjects is unrelated to its ability to reverse hypothermia in anesthetized rats. Additional experiments further investigated this unique and unexpected "anesthesia-specific" effect for TRPV1 antagonists. Such experiments demonstrated TRPV1 antagonists have an antihypothermic effect that is highly advantageous in a perioperative setting to inhibit and/or counterbalance anesthesia-induced hypothermia.

Moreover, experiments conducted herein demonstrated that antagonism of TRPV1 before the surgical insult reduces nociceptor sensitization and results in preemptive analgesia. Indeed, such experiments demonstrated that TRPV1 antagonists reversed anesthesia-induced hypothermia without causing hyperthermia when anesthesia is worn off. Moreover, it was shown that a single dose of TRPV1 antagonist given at anesthesia induction has a preemptive analgesic effect 24 hours post surgery.

Accordingly, the present invention provides compositions and methods for treating, ameliorating, and preventing anesthesia-induced hypothermia and postsurgical associated hyperalgesia in a mammalian subject comprising administering to the subject an effective amount of an ion channel TRPV1 inhibitor. In some embodiments, the methods comprise administering the TRPV1 inhibitor with additional agent(s), e.g., additional therapeutic agents or therapeutic techniques for preventing and treating anesthesia-induced hypothermia (e.g., warm blanket treatment, increased ambient temperature treatment).

In some embodiments, the compositions and methods of the present invention are used to treat an animal (e.g., a mammalian patient including, but not limited to, humans and veterinary animals) experiencing or at risk for experiencing anesthesia-induced hypothermia through administering to the animal an agent capable of preventing and/or diminishing anesthesia-induced hypothermia (e.g., an ion channel TRPV1 inhibitor). In this regard, various diseases and pathologies are amenable to treatment or prophylaxis using the present methods and compositions (e.g., any hypothermic condition associated with anesthesia).

Such methods are not limited to a particular type or kind of an agent capable of preventing and/or diminishing anesthesia-induced hypothermia (e.g., an ion channel TRPV1 inhibitor). In some embodiments, the agent capable of preventing and/or diminishing anesthesia-induced hypothermia is an ion channel TRPV1 inhibitor.

In some embodiments, the TRPV1 inhibitor is administered before, after, or simultaneous with administration of a general anesthesia. Examples of general anesthesia include inhalation anesthetics such as isoflurane, halothane, methoxyflurane and the like; intravenous anesthetics such as sodium thiopental, ketamine, propofol and the like; induction anesthetics used along with inhalation anesthetics; and combinations thereof.

Such methods are not limited to a particular type or kind of a TRPV1 inhibitor. In some embodiments, the TRPV1 inhibitor is capable of inhibiting TRPV1 activity and/or expression. Indeed, any suitable TRPV1 inhibitor or combination of inhibitors may be used in the methods and compositions herein. For example, a subject may be treated with a TRPV1 selective inhibitor and a nonselective TRPV1 inhibitor.

In some embodiments, the TRPV1 inhibitor is AMG 517 (see, e.g., Gavva, N R, et al., J. Pharmacol Exp Ther, 2007, 323(1), 128-137). In some embodiments, the TRPV1 inhibitor is civamide (zucapsaicin), ABT-102, GRC-6211, AZD1386, SB-705498, NGD 8243/MK-2295, JTS-653, JYL1421, JNJ 17203212, SAR-115740, KJM429, or capsazepine. Additional examples of TRPV1 inhibitors include, but are not limited to, N-(4-tertiarybutylphenyl)-4-(3-chloropyridin-2-yl)-tetrahydropyrazine-1 (2H)-carboxamide; N-(3-Methoxyphenyl)-4-chlorocinnamide; 1-Isoquinolin-5-yl-3-(4-trifluoromethyl-benzyl)-urea; (2E)-N-(2,3-Dihydro-1,4-benzodioxin-6-yl)-3-[4-(1,1-dimethylethyl)phenyl]-2-propenamide; 2-Acetylamino-4-[6'-(4-trifluoromethylphenyl)-pyrimidin-4'-yl-oxy]-benzothiazole; N-(2-bromophenyl-N'-[((R)-1-(5-trifluoromethyl-2-pyridyl)pyrrolidin-3-yl)]urea; N-(2-bromophenyl)-N'-{2-[ethyl(3-methylphenyl)amino]ethyl}urea; (R)-(5-tert-butyl-2,3-dihydro-1H-inden-1-yl)-3-(1H-indazol-4-yl)-urea; N-(Isoquinolin-5-yl)-N'-[spiro-(cyclobutane-1,2'-(3',4'-dihydro-benzopyran-4'-yl))]urea; (2R)-4-(3-chloro-2-pyridinyl)-2-methyl-N-[4-(trifluoromethyl)phenyl]-1-piperazinecarboxamide; 4-(4'-Trifluoromethyl-anilino)-7-(3'-trifluoromethyl-pyridin-2-yl)-quinazoline; N-[2-(4-chlorophenyl)ethyl]-1,3,4,5-tetrahydro-7,8-dihydroxy-2H-2-benzazepine-2-carbothioamide; (5R*,8R*,6E,9E)-5,8-Dimethyl-4-methylenetetradeca-6,9-dienoic acid; 1-(3-Fluorobenzyl)-2-

(N-(1,2-dimethyl-1,3-isoindazol-5-yl)-acetamido)-{pyridine-[3,4-b]-pyrrole}; N-(4-chlorobenzyl)-N'-(1-methyl-1H-indazol-4-yl)urea; N-(4-tert-butylbenzyl)-N'-(1-methyl-1H-indazol-4-yl)urea; N-(3-fluoro-4-(trifluoromethyl)benzyl)-N'-(1-methyl-1H-indazol-4-yl)-urea; N-(4-fluoro-3-(trifluoromethyl)benzyl)-N'-(1-methyl-1H-indazol-4-yl)-urea; N-(3,4-dichlorobenzyl)-N'-(1-methyl-1H-indazol-4-yl)urea; N-(2,4-dichlorobenzyl)-N'-(1-methyl-1H-indazol-4-yl)urea; N-(4-ethylbenzyl)-N'-(1-methyl-1H-indazol-4-yl)urea; N-(2-chlorobenzyl)-N'-(1-methyl-1H-indazol-4-yl)urea; N-(4-fluorobenzyl)-N'-(1-methyl-1H-indazol-4-yl)urea; N-(2-fluorobenzyl)-N'-(1-methyl-1H-indazol-4-yl)urea; N-[1-(bromophenyl)ethyl-N'-(1-methyl-1H-Indazol-4-yl)urea; N-(1-methyl-1H-indazol-4-yl)-N'-{4-[(trifluoromethyl)thio]benzyl}urea; 1-(2,3-dichlorophenyl)-3-[2-(N-ethyl-3-methylanilino)ethyl]urea; 1-[2-(N-ethyl-3-methylanilino)ethyl]-3-naphthalen-1-ylurea; 1-(4-bromophenyl)-3-[2-(N-ethyl-3-methylanilino)ethyl]urea; 1-(3-bromophenyl)-3-[2-(N-ethyl-3-methylanilino)ethyl]urea; 1-(chlorophenyl)-3-[2-(N-ethyl-3-methylanilino)ethyl]urea; 1-[2-(N-ethyl-3-methylanilino)ethyl]-3-(2-fluorophenyl)urea; 1-[2-{N-ethyl-3-methylanilino)ethyl]-3-(2-methylphenyl)urea; 1-[2-(N-ethyl-3-methylanilino)ethyl]-3-phenylurea; 2-[(2-bromophenyl)carbamoylamino]ethyl-ethylmethyl-(2-methylphenyl)azanium iodide; 1-(2-bromophenyl)-3-[2-(N-ethyl-3-fluoro-4-methylanilino)ethyl]urea; 1-(2-bromophenyl)-3-[2-(N-ethyl-3,4-difluoroanilino)ethyl]urea; 1-(2-bromophenyl)-3-[2-(N-ethyl-3-fluoroanilino)ethyl]urea; 1-(2-bromophenyl)-3-[2-(N-ethyl-4-methylanilino)ethyl]urea; 1-(2-bromophenyl)-3-[2-(N-ethyl-2-methylanilino)ethyl]urea; 1-(2-bromophenyl)-3-[2-(N-ethylanilino)ethyl]urea; N-[2-[(2-bromophenyl)carbamoylamino]ethyl]-N-(3-methylphenyl)acetamide; 1-[2-{N-benzyl-3-methylanilino)ethyl]-3-(2-bromophenyl)urea; 1-(2-bromophenyl)-3-[2-(2,3-dimethylanilino)ethyl]urea; 1-(2-bromophenyl)-3-[2-(3-methylanilino)ethyl]urea; 1-(2,5-dichlorophenyl)-3-[2-(N-ethyl-3-methylanilino)ethyl]urea; 4-fluoro-4-(3-methylpyridin-2-yl)-N-[4-trifluoromethylphenyl]piperidine-1-carboxamide; 4-fluoro-4(pyridin-2-yl)N-[4-trifluoromethylphenyl]piperidine-1-carboxamide; 4-fluoro-4(pyridine-2-yl)N-[4-trifluoromethylbenzyl]piperidine-1-carboxamide; 2-{4-fluoro-1-[4-trifluoromethylbenzoyl]piperidin-4-yl}pyridine; 2-(4-fluoro-1-{[4-trifluoromethylphenyl]acetyl}piperidin-4-yl)pyridine; 2-(4-fluoro-1-{3-[4-trifluoromethylphenyl]propanoyl}piperidin-4-yl)pyridine; 4-fluoro-4-(1-methyl-1H-imidazol-2-yl)-N-[4-trifluoromethylphenyl]piperidine-1-carboxamide; 4-methoxy-4-pyridin-2-yl-N-[4-trifluoromethylphenyl]piperidine-1-carboxamide; 4-methoxy-4-pyridin-2-yl-N-[4-trifluoromethylbenzyl]piperidine-1-carboxamide; 4-fluoro-N-(4-isopropylphenyl)-4-(3-methylpyridin-2-yl)piperidine-1-carboxamide; 4-fluoro-4-(3-methylpyridin-2-yl)-N-{4-[1,2,2,2-tetrafluoro-1-trifluoromethylethyl]phenyl}piperidine-1-carboxamide; N-(4-Tert-butylphenyl)-4-fluoro-4-(3-methylpyridin-2-yl)piperidine-1-carboxamide; 4-fluoro-4-(3-methylpyridin-2-yl)-N-[4-(pentafluoro-lambda(sup 6)-sulfanyl)phenyl]piperidine-1-carboxamide; N-(4-Butylphenyl)-4-fluoro-4-(3-methylpyridin-2-yl)piperidine-1-carboxamide; N-(4-Benzylphenyl)-4-fluoro-4-(3-methylpyridin-2-yl)piperidine-1-carboxamide; N-biphenyl-4-yl-4-fluoro-4-(3-methylpyridin-2-yl)piperidine-1-carboxamide; 4-fluoro-4-(3-methylpyridin-2-yl)-N-[5-trifluoromethylpyridin-2-yl]piperidine-1-carboxamide; 4-(3-chloropyridin-2-yl)-4-fluoro-N-[4-trifluoromethylphenyl]piperidine-1-carboxamide; 4-fluoro-4-(3-fluoropyridin-2-yl)-N-[4-trifluoromethylphenyl]piperidine-1-carboxamide; 4-fluoro-4-(3-methoxypyridin-2-yl)-N-[4-trifluoromethylphenyl]piperidine-1-carboxamide; 4-fluoro-4-(3-methylpyridin-2-yl)-N-[4-trifluoromethylphenyl]piperidine-1-carbothioamide; N'-cyano-4-fluoro-4-(3-methylpyridin-2-yl)-N-[4-trifluoromethylphenyl]piperidine-1-carboximidamide; 4-fluoro-4-(3-methylpyridin-2-yl)-N'-(1-phenylpiperidin-4-yl)-N-[4-trifluoromethylphenyl]piperidine-1-carboximidamide; 4-fluoro-4-phenyl-N-[4-trifluoromethylphenyl]piperidine-1-carboxamide; (+/−)-(syn)-4-fluoro-2-methyl-4-(3-methylpyridin-2-yl)-N-[4-trifluoromethylphenyl]piperidine-1-carboxamide; 4-(fluoromethyl)-4-pyridin-2-yl-N-[4-trifluoromethylphenyl]piperidine-1-carboxamide; syn- and anti-3-fluoro-3-pyridin-2-yl-N-[4-trifluoromethylphenyl]-8-azabicyclo[3.2.1]octane-8-carboxamide; 3-fluoro-3-pyridin-2-yl-N-[4-trifluoromethylphenyl]-8-azabicyclo[3.2.1]octane-8-carboxamide; 4-fluoro-4-pyrimidin-2-yl-N-[4-trifluoromethylphenyl]piperidine-1-carboxamide; 4-fluoro-4-(3-phenylpropyl)-N-[4-trifluoromethylphenyl]piperidine-1-carboxamide; 2-[4-fluoro-4-(3-methylpyridin-2-yl)piperidin-1-yl]-6-trifluoromethyl-1H-benzimidazole; 2-(4-fluoro-4-pyridin-2-ylpiperidin-1-yl)-6-(trifluoromethyl)-1H-benzimidazole; 4-fluoro-N-[4-trifluoromethyiphenyl]-4-[3-trifluoromethylpyridin-2-yl]piperidine-1-carboxamide; 4-fluoro-N-(4-methylphenyl)-4-(3-methylpyridin-2-yl)piperidine-1-carboxamide; N-(4-ethylphenyl)-4-fluoro-4-(3-methylpyridin-2-yl)piperidine-1-carboxamide; N-(4-chlorophenyl)-4-fluoro-4-(3-methylpyridin-2-yl)piperidine-1-carboxamide; 4-fluoro-4-(3-methylpyridin-2-yl)-N-[4-trifluoromethoxyphenyl]piperidine-1-carboxamide; N-(4-cyanophenyl)-4-fluoro-4-(3-methylpyridin-2-yl)piperidine-1-carboxamide; N-[4-dimethylaminophenyl]-4-fluoro-4-(3-methylpyridin-2-yl)piperidine-1-carboxamide; 1-(2-(3,3-dimethylbutyl)-4-(trifluoromethyl)benzyl)-3-(1-methyl-1H-indazo-1-4-yl)urea; N-acetyl-1-phenylalanyl-1-leucinamide; and pharmaceutically acceptable salts thereof.

In some embodiments, the TRPV1 antagonist is selected from AMG 517, capsazepine, SB-366791, AMG 9810, and/or ABT-102.

Use of opioid based therapeutics prior to a surgical purpose has been shown in some instances to produce a paradoxical hyperalgesic response post surgery (see, e.g., Kim, et al., Front Pharmacol 2014, 5:108). Indeed, while opioid based therapeutics are strong analgesics, such therapeutics do not provide high amounts of preemptive analgesia (see, e.g., Ong, et al., Anesth. Analg. 2005; 100:757-73). Experiments conducted during the course of developing embodiments for the present invention, however, determined that preemptive administration of a TRPV1 antagonist provides an opioid sparing effect on postsurgical hyperalgesia.

As such, in certain embodiments, methods for preventing and/or diminishing postsurgical hyperalgesia in a subject are provided. For example, in some embodiments, such methods comprise administration of a TRPV1 antagonist prior to surgical onset for purposes of preventing and/or diminishing pain (e.g., hyperalgesia) experienced post-surgery. Such methods are not limited to a particular subject. In some embodiments, the subject is a human being or a veterinary animal about to undergo a surgical procedure likely to result in postsurgical hyperalgesia. Such methods are not limited to a particular TRPV1 antagonist. Indeed, any TRPV1 antagonist described herein may be utilized (e.g., AMG 517, capsazepine, SB-366791, AMG 9810, and/or ABT-102).

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, of the body weight per day. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example. The unit dose may be administered one or more times daily as one or more tablets or capsules each containing from about 0.01 to about 100 mg, conveniently about 0.25 to 50 mg of the compound or its solvates.

In a topical formulation, the compound may be present at a concentration of about 0.01 to 100 mg per gram or milliliter of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient who may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

FIG. 1 shows the effect of TRPV1 antagonism (e.g., AMG 517) on volatile anesthesia-induced hypothermia. Briefly, after obtaining baseline core body temperature, lightly restrained rats were anesthetized with isoflurane (5% induction, 2.5% maintenance), the effect of varying dose of AMG 517 (0.01, 0.1 and 1 mg/kg) and control (vehicle) on rectally-measured temperature (core body temperature) was measured at 5 min intervals. At 20 minutes, a warming blanket was used to prevent further temperature drop in the control (vehicle) group. Vehicle treated rats developed hypothermia after exposure to anesthesia. However, AMG 517 dose dependently reversed anesthesia-induced hypothermia with the doses of 0.1 and 1 mg/kg being statistically significant at all time points tested (p<0.01, two way ANOVA with Tukey's posthoc analysis).

Figure 2:
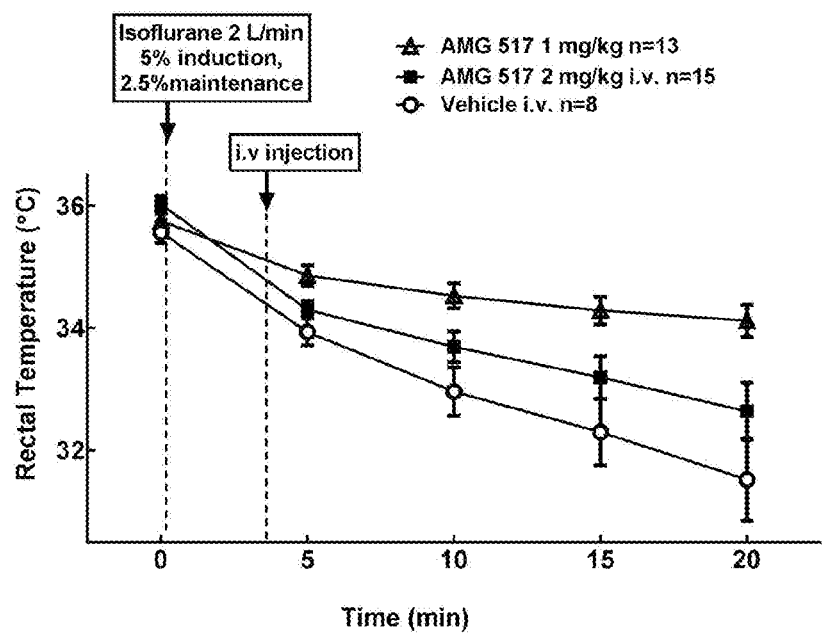
FIG. 2 shows the effect of TRPV1 antagonism (e.g., AMG 517) on anesthesia-induced hypothermia with neonatal rats.

FIG. 2 shows the effect of TRPV1 antagonism (e.g., AMG 517) on anesthesia-induced hypothermia with neonatal rats. Briefly, after gently separating neonatal male or female rats (age 10d) from the littermates, the animals were exposed to isoflurane anesthesia (5% induction, 2.5% maintenance), and then were injected with either vehicle or AMG 517 (1-2 mg/kg, i.v.) and core body temperature was measured at 5 minute intervals. Vehicle treated neonates demonstrated a substantial drop in core body temperature with the maximal drop seen at 20 minute post anesthesia induction at 32° C. AMG 517 partially and statistically significantly (p<0.01, two way ANOVA with Tukey's posthoc analysis) reversed anesthesia-induced hypothermia at 1 mg/kg dose (at 20 min time point) and 2 mg/kg dose at all time points tested.

Example II

Figure 3:
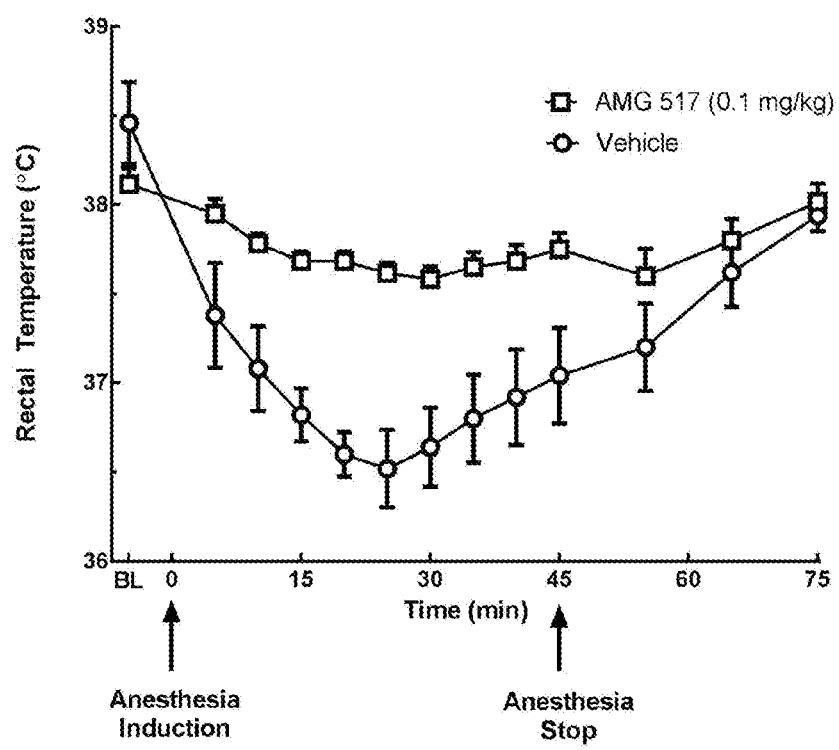
FIG. 3 shows the effect of AMG 517 and control (vehicle) on temperature as a function of time at prior to anesthesia induction, anesthesia induction, anesthesia stop, and post anesthesia period. The data demonstrate that AMG 517 does not produce hyperthermia in the post-anesthesia period.

After taking baseline core body temperature, rats were anesthetized with isoflurane and quickly injected with either vehicle or 0.1 mg/kg of AMG 517 via a tail vein injection. The core body temperature was measured every 5 minutes during the duration of anesthesia (45 min) and 30 minutes after that (n=8 per group) (see, FIG. 3). The vehicle treated rats demonstrated anesthesia induced hypothermia immediately after anesthesia induction that persisted throughout anesthesia and took another 30 minutes to reach normothermia after anesthesia was turned off. AMG 517 treated rats never developed hypothermia throughout the anesthesia period. Importantly, AMG 517 did not cause hyperthermia even when the animals recovered from anesthesia.

Figure 4:
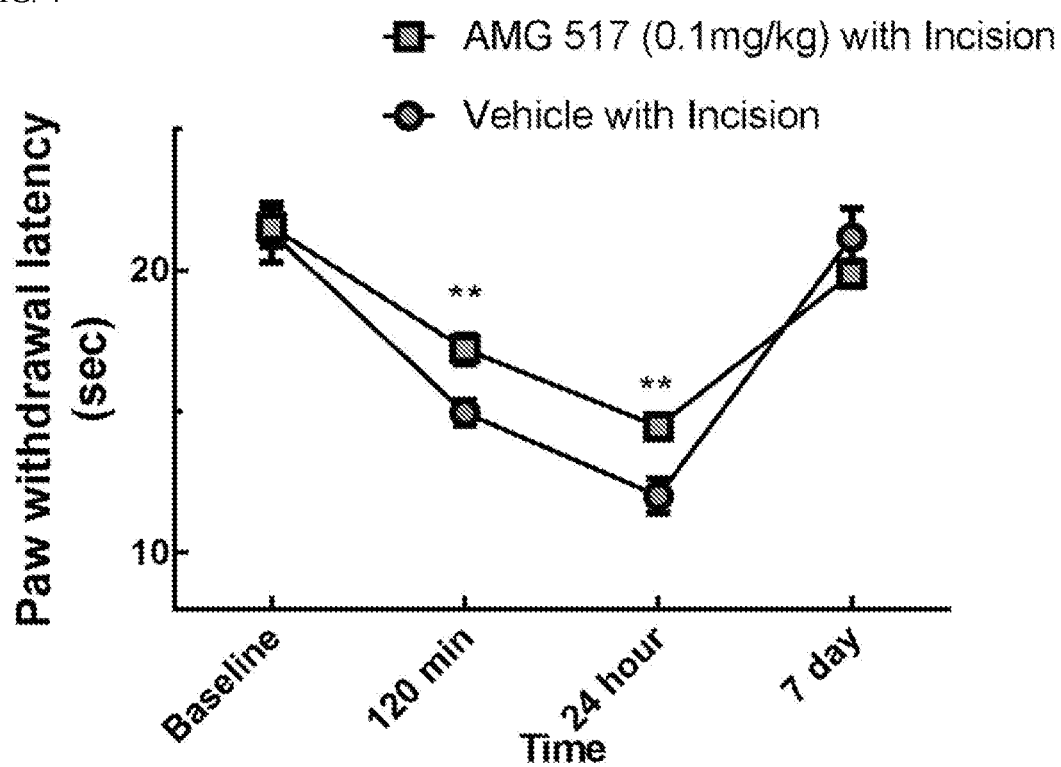
FIG. 4 shows the effect of AMG 517 and control (vehicle) on thermal pain sensitivity as a function of time at baseline, 120 minutes post surgery, 24 hours post surgery, and 7 days post surgery. A single preemptive dose of AMG 517 (0.1 mg/kg) or vehicle was administered before hindpaw incision was performed and thermal hyperalgesia was measured at various time points post surgery. Data were analyzed using two-way ANOVA with Bonferroni posthoc test (n=6-8 per group, ** denotes p<0.01)

Baseline thermal withdrawal thresholds were obtained in rats. Next, using same protocol as FIG. 3, rats received either vehicle or AMG 517 0.1 mg/kg at anesthesia induction. Then a small incision was performed on the hindpaw and closed. Thermal withdrawal latency were obtained at 2 hours, 24 hours and 7 days post surgery. Data were analyzed using two-way ANOVA with Bonferroni posthoc test (n=6-8 per group, ** denotes p<0.01) (see, FIG. 4).

Example III

Figure 5:
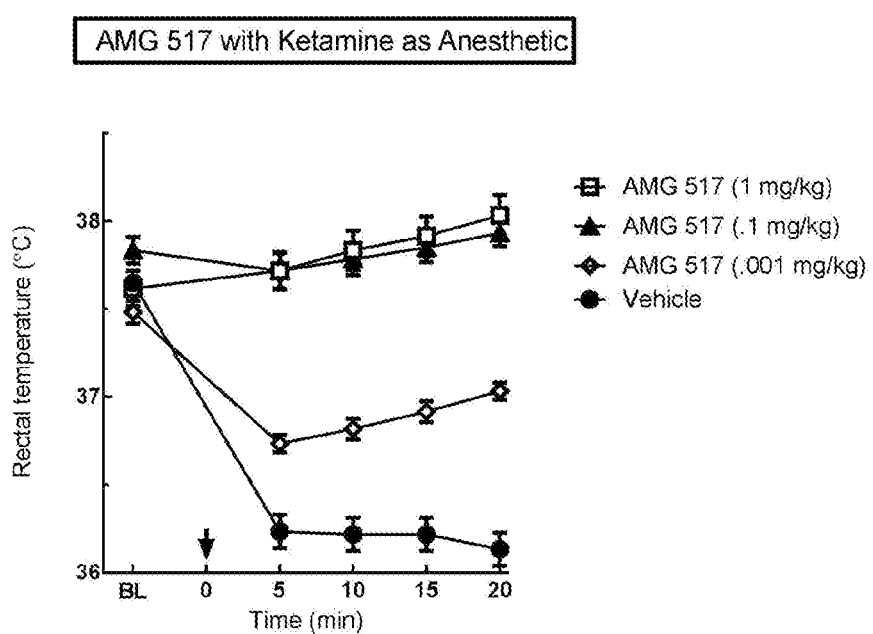
FIG. 5 shows the effect of administration \varying dosage levels of a TRPV1 antagonist (e.g., AMG 517) on a non-volatile anesthetic (ketamine)-induced hypothermia.

This example describes the use of AMG 517 to reverse hypothermia induced by a non-volatile anesthetic (ketamine) (FIG. 5). After taking baseline core body temperature, rats were anesthetized with ketamine (100 mg/kg) and quickly injected with either vehicle or 0.01-1 mg/kg of AMG 517 via a tail vein injection. The core body temperature was measured every 5 minutes for 20 minutes post ketamine injection (n=8 per group). FIG. 5 shows the results with AMG 517 dose dependently and statistically significantly (p<0.01, two way ANOVA with Tukey's posthoc analysis) reversed ketamine-induced hypothermia without causing hyperthermia at all time points tested. This example demonstrates that the ability of TRPV1 antagonist to reverse anesthesia induced hypothermia is not limited to only volatile anesthetics but also extends to intravenous anesthetics.

Example IV

This example demonstrates that preemptive administration of TRPV1 antagonist has opioid sparing effect on postsurgical pain.

Poor postsurgical pain control results in increased suffering, diminished function, hospital related complications including infections, cardiovascular issues and bleeding, all leading to longer in-hospital stays (see, e.g., Rathmell, J. P., et al., Reg Anesth Pain Med, 2006. 31(4 Suppl 1): p. 1-42; Thomas, T., et al., Pain, 1998. 75(2-3): p. 177-85). Moreover, a strong link exists between acute postsurgical pain intensity and the risk of development of chronic pain (see, e.g., Kehlet, H., T. S. Jensen, and C. J. Woolf, Lancet, 2006. 367(9522): p. 1618-25). Management of postoperative pain relies primarily on opioids and nonsteroidal anti-inflammatory drugs (NSAIDs). Excessive opioid use in the perioperative phase is associated with increased neurological and respiratory morbidities (see, e.g., Kehlet, H. and K. Holte, Br J Anaesth, 2001. 87(1): p. 62-72). NSAIDs cause increased bleeding, and negatively affect bone healing and kidney function (see, e.g., Souter, A. J., B. Fredman, and P. F. White, Anesth Analg, 1994. 79(6): p. 1178-90). Unlike many other pain conditions (e.g. traumatic fracture, chronic low back pain), in postsurgical pain, the timing of tissue injury is known ahead of time. This fundamental difference can be exploited to preemptively block or reduce nociceptive input during the surgical insult to decrease the severity and duration of postsurgical pain. Multiple such preemptive analgesia techniques have been tried with varying success. TRPV1 has be demonstrated to be one of the key protein involved in inflammatory hyperalgesia. Administration of TRPV1 antagonists upon anesthesia induction can reduce nociceptor sensitization during surgical insult and in turn reduce postoperative opioid requirement.

Experiments were conducted wherein the investigator was blinded to treatment allocations during the behavior testing. Baseline thermal and mechanical withdrawal latencies were obtained using a Hargreaves apparatus (see, e.g., Hargreaves, K., et al., Pain, 1988. 32(1): p. 77-88) and Von Frey filaments (see, e.g., Chaplan, S. R., et al., J Neurosci Methods, 1994. 53(1): p. 55-63) at least 24 hours prior to the surgery. The animals were anesthetized using isoflurane as described above and treated with either vehicle or TRPV1 antagonist via the tail vein injection prior to performing the surgery for incisional pain (see, e.g., Brennan, T. J., E. P. Vandermeulen, and G. F. Gebhart, Pain, 1996. 64(3): p. 493-501).

Assessment of thermal and mechanical hyperalgesia was performed at 24 hours post surgery. Rats received varying doses of subcutaneous morphine and either preemptive TRPV1 antagonist or vehicle treatment. Analgesic responses were measured in both groups of animals.

Data were converted to % MPE (maximal possible effect) by the formula: % MPE=100×(test latency-control latency)/(10-control latency).

Figure 6:
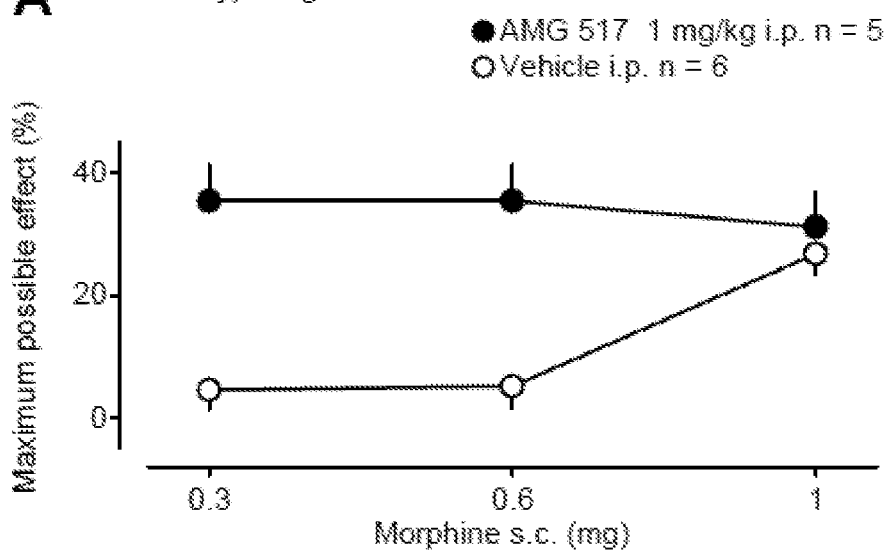
FIG. 6 shows the opioid sparing effect of AMG 517 compared to control (vehicle) on postsurgical A) thermal hyperalgesia, and B) on mechanical hyperalgesia.
Figure 6:
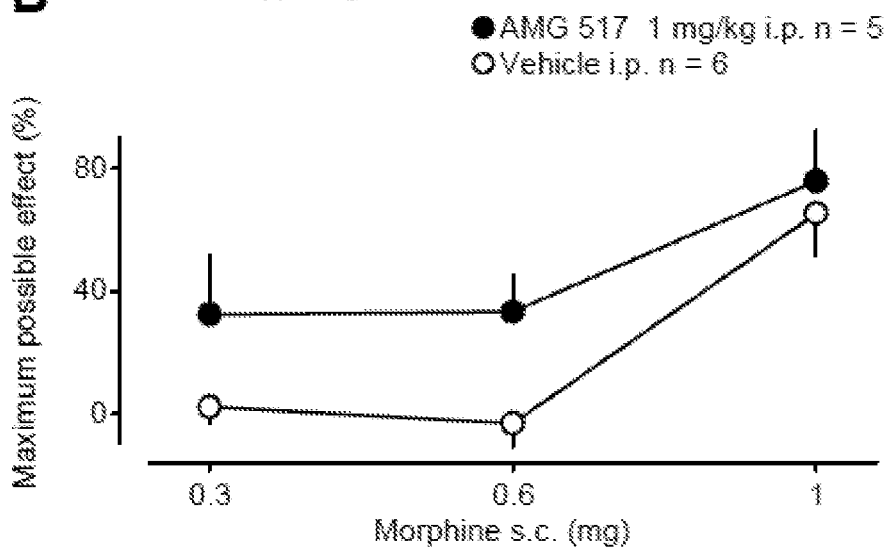

FIG. 6 shows the effect of AMG 517 and control (vehicle) on morphine reversal of A) thermal hyperalgesia, and B) mechanical hyperalgesia.

In vehicle treated animals, the postsurgical pain assessed by two different measures, thermal and mechanical hyperalgesia was not responsive to morphine until the dose of morphine was raised to 1 mg/kg. However, in animals that received preemptive TRPV1 antagonist treatment before the surgical insult, morphine demonstrated analgesic effect at much lower doses of 0.3 and 0.6 mg/kg.

The results demonstrate that preemptive TRPV1 antagonist has an opioid-sparing effect on postsurgical pain. Given that decreased opioid use in the postsurgical pain has been associated with faster recovery and significantly less morbidity, preemptive analgesia by TRPV1 antagonist may have a huge impact on perioperative outcomes.

Example V

This example demonstrates that regardless of whether specific TRPV1 antagonists cause or do not cause hyperthermia in unanesthetized animals, such TRPV1 antagonists still dose dependently reverse anesthesia-induced hypothermia.

After acclimatizing to the testing chamber and obtaining baseline core body temperature, adult rats were anesthetized with isoflurane (2 L/min, 5% induction, 2.5% maintenance) and the anesthetized animals were injected with vehicle or various TRPV1 antagonists at doses described and rectal temperature was monitored for 20 minutes post anesthesia-induction.

Figure 7:
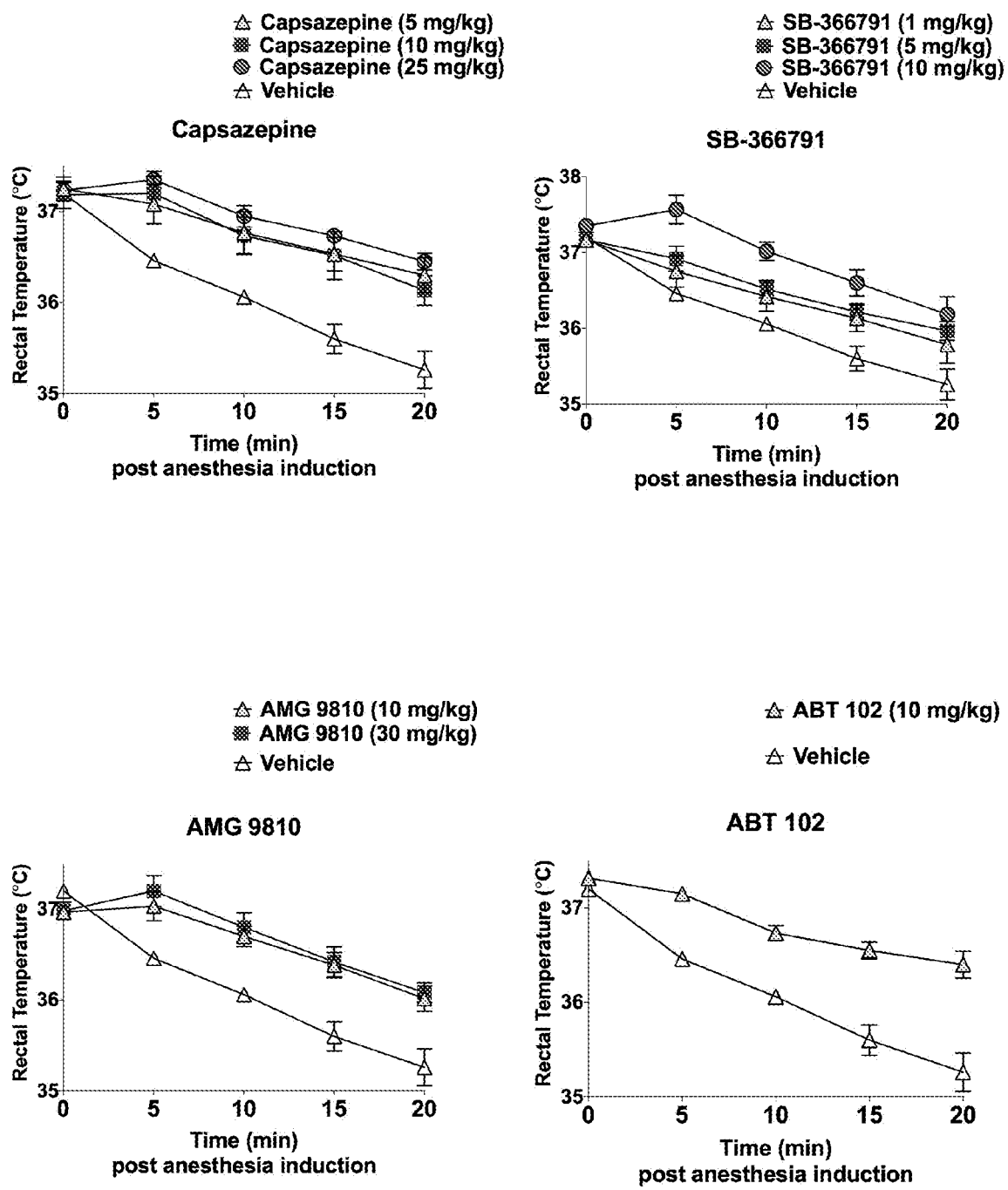
FIG. 7 shows the effect of TRPV1 antagonism on anesthesia-induced hypothermia with varying dosage levels of capsazepine, SB366791, AMG 9810, and ABT 102.

The data demonstrated that regardless whether the antagonists cause hyperthermia in unanesthetized rats (SB, AMG and ABT compounds) or don't (capsazepine), such TRPV1 antagonists still dose dependently reverse anesthesia-induced hypothermia (see, FIG. 7).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of preventing anesthesia-induced hypothermia in a mammalian subject in need thereof, comprising administering to the subject an ion channel TRPV1 inhibitor before or during an induction phase of anesthesia, wherein anesthesia-induced hypothermia is caused by administration of general anesthesia selected from at least one of an inhalation anesthetic or an intravenous anesthetic and wherein the ion channel TRPV1 inhibitor is selected from the group consisting of capsazepine, SB-366791, and A-1165442.

2. The method of claim 1, wherein the general anesthetic is selected at least one of from isoflurane, sevoflurane, desflurane, halothane, methoxyflurane, sodium thiopental, ketamine, and propofol.

3. The method according to claim 1, wherein the TRPV1 antagonist is administered intravenously, orally, or both.

4. The method according to claim 1, wherein the TRPV1 inhibitor is administered before a beginning of a maintenance phase of anesthesia.

5. The method according to claim 1, wherein the administration of the TRPV1 inhibitor prevents anesthesia-induced hypothermia during an induction phase of general anesthesia.

* * * * *